(12) United States Patent
Gross et al.

(10) Patent No.: US 8,551,191 B2
(45) Date of Patent: Oct. 8, 2013

(54) DICATIONIC 4-AZA-1-AZONIABICYCLO[2.2.2]OCTANES AND AGENTS FOR COLOURING KERATIN-CONTAINING FIBERS

(71) Applicant: Henkel AG & Co. KGaA, Duesseldorf (DE)

(72) Inventors: Wibke Gross, Hueckelhoven (DE); Helmut Giesa, Meerbusch (DE); Astrid Kroos, Monheim (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/784,296

(22) Filed: Mar. 4, 2013

(65) Prior Publication Data

US 2013/0180542 A1      Jul. 18, 2013

Related U.S. Application Data

(63) Continuation of application No. PCT/EP2011/058791, filed on May 30, 2011.

(30) Foreign Application Priority Data

Oct. 20, 2010   (DE) .......................... 10 2010 042 696

(51) Int. Cl.
*A61Q 5/10* (2006.01)
*C07D 233/00* (2006.01)

(52) U.S. Cl.
USPC ............... 8/405; 8/406; 8/437; 8/451; 8/565; 8/566; 8/570; 8/573; 548/317.1

(58) Field of Classification Search
USPC ............. 8/405, 406, 437, 451, 565, 566, 570, 8/573; 548/317.1
See application file for complete search history.

(56) References Cited

U.S. PATENT DOCUMENTS 7,060,110 B2 *  6/2006  Vidal et al. ..................... 8/405
2006/0037151 A1   2/2006  Lagrange

FOREIGN PATENT DOCUMENTS

WO          02078658 A1    10/2002
WO        2007144280 A2    12/2007

OTHER PUBLICATIONS

STIC Search Report dated May 15, 2013.*
European Patent Office, International Searching Authority, "International Search Report" mailed Jan. 25, 2012; International Appln. No. PCT/EP2011/058791, filed May 30, 2011.
European Patent Office, International Searching Authority, "Written Opinion" mailed Jan. 25, 2012; International Appln. No. PCT/EP2011/058791, filed May 30, 2011.

* cited by examiner

*Primary Examiner* — Eisa Elhilo
(74) *Attorney, Agent, or Firm* — Krista A. Kostiew

(57) ABSTRACT

Dicationic azo dyes of the formula (I), which are suitable for coloring keratin fibers, in particular human hair, and are in part themselves still not described in the prior art are provided. In colorations, particularly brilliant and luminous red shades are obtained. Agents for dyeing and optionally simultaneously lightening keratin fibers and methods for dyeing and optionally simultaneously lightening keratinic fibers also are provided.

20 Claims, No Drawings

DICATIONIC 4-AZA-1-AZONIABICYCLO[2.2.2]OCTANES AND AGENTS FOR COLOURING KERATIN-CONTAINING FIBERS

CROSS-REFERENCE TO RELATED APPLICATION

This is a continuation of International Application No. PCT/EP2011/058791 filed May 30, 2011, which was published under PCT Article 21(2) and which claims priority to German Application No. 102010042696.2, filed Oct. 20, 2010, which are all hereby incorporated in their entirety by reference.

TECHNICAL FIELD

The technical field relates to novel cationic dyes as well as to agents for dyeing and optionally simultaneously lightening keratin-containing fibers, especially human hair, the agents comprising these dyes, the use of these cationic dyes for dyeing hair as well as a method for dyeing keratin-containing fibers, especially human hair. Generally, either substantive dyes or oxidation dyes that result from oxidative coupling of one or more developer components with each other or with one or more coupler components are used for dyeing fibers containing keratin. Coupler components and developer components are also called oxidation dye precursors.

BACKGROUND

Normally, primary aromatic amines with an additional free or substituted hydroxyl or amino group in the para or ortho position, diaminopyridine derivatives, heterocyclic hydrazones, 4-amino pyrazole derivatives as well as 2,4,5,6-tetramino pyrimidine and derivatives thereof are employed as the developer components.

Specific exemplary representatives are p-phenylenediamine, p-toluoylenediamine, 2,4,5,6-tetraminopyrimidine, p-amino phenol, N,N-bis(2-hydroxyethyl)-p-phenylenediamine, 2-(2,5-diaminophenyl)ethanol, 2-(2,5-diaminophenoxy)ethanol, 1-phenyl-3-carboxyamido-4-amino-pyrazolone-5,4-amino-3-methylphenol, 2-aminomethyl-4-aminophenol, 2-hydroxymethyl-4-aminophenol, 2-hydroxy-4,5,6-triaminopyrimidine, 2,4-dihydroxy-5,6-diamino pyrimidine, 2,5,6-triamino-4-hydroxypyrimidine and 4,5-diamino-1-(2-hydroxyethyl)pyrazole.

m-Phenylenediamine derivatives, naphthols, resorcinol and resorcinol derivatives, pyrazolones, m-amino phenols and substituted pyridine derivatives are generally used as the coupling components.

Particularly suitable coupling substances are α-naphthol, 1,5-dihydroxynaphthalene, 2,7-dihydroxynaphthalene and 1,7-dihydroxynaphthalene, 5-amino-2-methylphenol, m-amino phenol, resorcinol, resorcinol monomethyl ether, m-phenylenediamine, 2,4-diamino phenoxyethanol, 2-amino-4-(2-hydroxyethylamino)-anisole (Lehmann's Blue), 1-phenyl-3-methylpyrazolone-5,2,4-dichloro-3-aminophenol, 1,3-bis(2,4-diaminophenoxy)propane, 2-chlororesorcinol, 4-chlororesorcinol, 2-chloro-6-methyl-3-amino phenol, 2-methylresorcinol, 5-methylresorcinol, 3-amino-6-methoxy-2-methylamino pyridine and 3,5-diamino-2,6-dimethoxypyridine.

Indeed, with the oxidation dyes, intensive colorations can be achieved with good fastness characteristics, but the development of the color normally occurs in the presence of oxidizing agents, such as e.g., $H_2O_2$, which in some cases can result in damage to the fibers. Furthermore, some oxidation dye precursors or certain mixtures of oxidation dye precursors sometimes have a sensitizing effect on people with delicate skin. Substantive dyes are applied under more gentle conditions, but their disadvantage is that the colorations often possess only inadequate fastness characteristics.

An advantage when dyeing hair with substantive dyes lies principally in the vibrant fashion shades that can be achieved with this dyeing method. For consumers with darker hair colorations, however, a lightening has to take place at the same time as the fashion shade dyeing, thereby lightening the natural hair color by destroying the melanin pigments of the original hair and thus lending more brilliance to the added dyes. The use of hydrogen peroxide by itself suffices for a slight lightening, however a combination of hydrogen peroxide and persulfate salts is usually added for stronger lightening over a plurality of nuances. Up to now, the person skilled in the art is aware of very few brilliant dyes from the prior art which are sufficiently stable towards hydrogen peroxide/persulfate salts and which simultaneously possess good applications-related properties.

SUMMARY

Accordingly, at least one object herein is to provide novel substantive dyes that dye the hair in particularly vibrant nuances, especially red nuances. In addition, these novel substantives should not be sensitizing and should possess good fastness characteristics. The focus resides particularly in the discovery of novel substantives that are highly stable towards oxidizing agents, such as hydrogen peroxide, and especially to the combination of hydrogen peroxide and persulfate salts. Moreover, the substantives should also possess other important fastness properties, such as for example, a good requirement profile in regard to wash fastness, perspiration fastness, and rubbing fastness.

It has now been found in an unforeseeable manner that compounds of the general Formula (I) are very well suited for the intensive dyeing of hair in vibrant red nuances. Surprisingly the inventive compounds are not only stable towards oxidation but also possess outstanding properties in regard to their wash fastness, perspiration fastness and rubbing fastness.

DETAILED DESCRIPTION

Dyes that comprise compounds of the following Formula (I) as well as some of the corresponding compounds themselves are hitherto unknown.

An exemplary embodiment provides agents for dyeing and optionally simultaneously lightening keratin fibers, especially human hair, comprising a dicationic azo dye of the Formula (I):

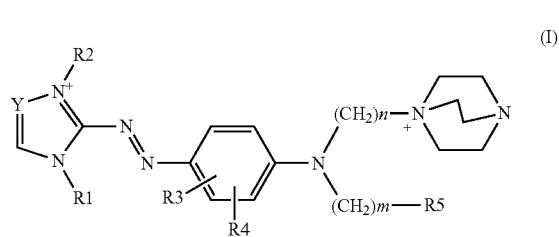

2 X⁻ in which

Y stands either for =CH— or a nitrogen atom, $R^1$, $R^2$ stand independently of one another for a $C_1$-$C_6$ alkyl group, a $C_2$-$C_6$ alkenyl group, a hydroxy $C_1$-$C_6$ alkyl group, a polyhydroxy $C_2$-$C_6$ alkyl group, a $C_1$-$C_6$ alkoxy $C_2$-$C_6$ alkyl group, a cyano $C_1$-$C_6$ alkyl group, an aryl group or an aryl $C_1$-$C_6$ alkyl group, $R^3$, $R^4$ stand independently of one another for a hydrogen atom, a $C_1$-$C_6$ alkyl group, a halogen atom (fluorine, chlorine, bromine or iodine), a $C_1$-$C_6$ alkoxy group, an amino group, a $C_1$-$C_6$ alkylamino group, a di-$C_1$-$C_6$ alkylamino group, a hydroxyl group or that $R^3$ and $R^4$ together form a 5-, 6- or 7-membered, saturated or unsaturated ring that can optionally comprise additional heteroatoms or can carry additional substituents, n, m stand independently of one another for a whole number from 1 to 6, $R^5$ stands for a hydrogen atom, a $C_1$-$C_6$ alkoxy group, a halogen atom (fluorine, chlorine, bromine or iodine), a hydroxyl group, a $C_1$-$C_6$ alkoxy-$C_2$-$C_6$ alkyloxy group, a nitrile group, an aryl group or a heteroaryl group, $X^-$ stands for a monovalent anion, for example, for halide, hydrogen sulfate, ½ sulfate, benzene sulfonate, p-toluene sulfonate, acetate, citrate, lactate, tetrafluoroborate, trifluoromethane sulfonate, or hexafluorophosphate.

Keratin-containing fibers are understood to mean wool, furs, feathers and particularly human hair. However, the inventive dyes can, in principle, also be used for dyeing other natural fibers, such as e.g. cotton, jute, sisal, linen or silk, modified natural fibers, such as e.g., cellulose regenerate, nitrocellulose, alkyl cellulose or hydroxyalkyl cellulose or acetyl cellulose. The inventively used term, "dyeing keratin fibers" includes any form of color change of the fibers. The included color changes are in particular those under the terms, tinting, blonding, oxidative dyeing, semi-permanent dyeing, permanent dyeing as well as temporary dyeing. Explicitly inventively included here are color changes that exhibit a lighter color result in comparison to the starting color, such as for example blonding.

Examples of $C_1$-$C_6$ alkyl groups are the methyl, ethyl, propyl, isopropyl, n-butyl, sec-butyl and tert.-butyl, n-pentyl and n-hexyl groups. Propyl, ethyl and methyl are preferred alkyl groups. Examples of suitable cyclic alkyl groups are cyclopentyl and cyclohexyl.

Examples of preferred $C_2$-$C_6$ alkenyl groups are vinyl and allyl.

Furthermore, as preferred examples of a $C_1$-$C_6$ monohydroxyalkyl group may be cited a hydroxymethyl, a 2-hydroxyethyl, a 2-hydroxypropyl, a 3-hydroxypropyl, a 4-hydroxybutyl group, a 5-hydroxypentyl and a 6-hydroxyethyl group. A 2-hydroxyethyl group is particularly preferred.

Exemplary $C_2$ to $C_6$ polyhydroxyalkyl groups are the 2,3-dihydroxypropyl group, 3,4-dihydroxybutyl group and the 2,4-dihydroxybutyl group.

Exemplary $C_1$ to $C_6$ alkoxy groups are a methoxy or an ethoxy group.

The methoxyethyl, ethoxyethyl, methoxypropyl, methoxybutyl, ethoxybutyl and the methoxyhexyl groups are examples of the inventive $C_1$-$C_6$ alkoxy $C_2$-$C_6$ alkyl groups.

A preferred hydroxy ($C_1$-$C_6$) alkoxy group is the 2-hydroxyethoxy group.

Exemplary halogen atoms are F, Cl, Br or I atoms, Br or Cl atoms being quite particularly preferred.

The aminomethyl, 2-aminoethyl, 3-aminopropyl, 2-dimethylaminoethyl, diethylaminomethyl, dimethylaminomethyl, 2-methylaminoethyl, dimethylamino, 1-piperidinomethyl, 1-pyrrolidinomethyl, 4-morpholinomethyl, bis(2-hydroxyethyl)amino and the amino group are examples of a group $R^5R^6N$—$(CH_2)_n$—, wherein the diethylaminomethyl, 1-piperidinomethyl, 2-dimethylaminoethyl, dimethylamino and the amino group are particularly preferred.

In an exemplary embodiment, the $R^1$ and $R^2$ groups, independently of one another, stand for a $C_1$-$C_6$ alkyl group, a $C_2$-$C_6$ alkenyl group, a cyano-$C_1$-$C_6$ alkyl group or an aryl $C_1$-$C_6$ alkyl group. It is particularly preferred when $R^1$ and $R^2$ both stand for a $C_1$-$C_6$ alkyl group (especially a methyl or ethyl group), a $C_2$-$C_6$ alkenyl group (especially an allyl group), or an aryl $C_1$-$C_6$ alkyl group (especially a benzyl group).

Inventive agents for dyeing and optionally simultaneously lightening keratinic fibers which comprise compounds of the Formula (I), in which the groups $R^1$ and $R^2$ stand for a $C_1$-$C_6$ alkyl group (in particular a methyl or ethyl group), a $C_2$-$C_6$ alkenyl group (in particular an allyl group) or an aryl $C_1$-$C_6$ alkyl group (in particular a benzyl group) are preferred embodiments.

Furthermore, compounds of the general Formula (I), in which $R^3$ and $R^4$ independently of one another stand for a hydrogen atom, a $C_1$-$C_6$ alkyl group, a halogen atom (fluorine, chlorine, bromine or iodine) or a $C_1$-$C_6$ alkoxy group, are particularly suitable for fulfilling the defined object. Compounds are particularly preferred here in which both $R^3$ as well as $R^4$ stand for a hydrogen atom, n preferably stands for the numbers 2 or 3, m preferably stands for the numbers 1, 2 or 3.

If $R^5$ stands for a hydrogen atom, a $C_1$-$C_6$ alkoxy group, a nitrile group or an aryl group, then this is likewise preferred. In this context, compounds of the general Formula (I), in which $R^5$ stands for a hydrogen atom, are quite particularly preferred.

The inventive compounds of the general Formula (I) concern dicationic compounds, whose positive charges are neutralized by a corresponding number of negative charges of the counter ion X. Neutralization can result from the presence of two single negatively charged counter ions (2 $X^-$), but the neutralization by a doubly negatively charged counter ion ($X^{2-}$) is also inventive.

In the context of a first embodiment, Y stands for a nitrogen atom.

Within this first embodiment, particularly suitable agents for dyeing and optionally lightening hair comprise a compound selected from the group of the Salts of 1,4-dimethyl-5-[(4-{methyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(4-{propyl[2-(4-aza-1-azoniabicyclo[2.2.2]octan-1-yl)ethyl]amino}phenyl)diazenyl]-4H-1,2,4-triazol-1-ium;

Salts of 1,4-diethyl-5-[(4-{methyl[2-(4-aza-1-azoniabicyclo[2.2.2]octan-1-yl)ethyl]amino}phenyl)diazenyl]-4H-1,2,4-triazol-1-ium;

Salts of 1,4-diethyl-5-[(4-{ethyl[2-(4-aza-1-azoniabicyclo[2.2.2]octan-1-yl)ethyl]amino}phenyl)diazenyl]-4H-1,2,4-triazol-1-ium;

Salts of 1,4-diethyl-5-[(4-{propyl[2-(4-aza-1-azoniabicyclo[2.2.2]octan-1-yl)ethyl]amino}phenyl)diazenyl]-4H-1,2,4-triazol-1-ium;

Salts of 1,4-diallyl-5-[(4-{methyl[2-(4-aza-1-azoniabicyclo[2.2.2]octan-1-yl)ethyl]amino}phenyl)diazenyl]-4H-1,2,4-triazol-1-ium;

Salts of 1,4-diallyl-5-[(4-{ethyl[2-(4-aza-1-azoniabicyclo[2.2.2]octan-1-yl)ethyl]amino}phenyl)diazenyl]-4H-1,2,4-triazol-1-ium;

Salts of 1,4-diallyl-5-[(4-{propyl[2-(4-aza-1-azoniabicyclo[2.2.2]octan-1-yl)ethyl]amino}phenyl)diazenyl]-4H-1,2,4-triazol-1-ium;

Salts of 1,4-dibenzyl-5-[(4-{methyl[2-(4-aza-1-azoniabicyclo[2.2.2]octan-1-yl)ethyl]amino}phenyl)diazenyl]-4H-1,2,4-triazol-1-ium;

Salts of 1,4-dibenzyl-5-[(4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dibenzyl-5-[(4-{propyl[2-(4-aza-1-azoniabicyclo[2.2.2]octan-1-yl)ethyl]amino}phenyl)diazenyl]-4H-1,2,4-triazol-1-ium Salts of 1,4-dimethyl-5-[(2-methyl-4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(2-methoxy-4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(2-chloro-4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(4-{methyl[3-(4-aza-1-azoniabicyclo[2.2.2]octan-1-yl)propyl]amino}phenyl)diazenyl]-4H-1,2,4-triazol-1-ium;

Salts of 1,4-dimethyl-5-[(4-{ethyl[3-(4-aza-1-azoniabicyclo[2.2.2]octan-1-yl)propyl]amino}phenyl)diazenyl]-4H-1,2,4-triazol-1-ium;

Salts of 1,4-dimethyl-5-[(4-{propyl[3-(4-aza-1-azoniabicyclo[2.2.2]octan-1-yl)propyl]amino}phenyl)diazenyl]-4H-1,2,4-triazol-1-ium;

Salts of 1,4-diethyl-5-[(4-{methyl[3-(4-aza-1-azoniabicyclo[2.2.2]octan-1-yl)propyl]amino}phenyl)diazenyl]-4H-1,2,4-triazol-1-ium;

Salts of 1,4-diethyl-5-[(4-{ethyl[3-(4-aza-1-azoniabicyclo[2.2.2]octan-1-yl)propyl]amino}phenyl)diazenyl]-4H-1,2,4-triazol-1-ium;

Salts of 1,4-diethyl-5-[(4-{propyl[3-(4-aza-1-azoniabicyclo[2.2.2]octan-1-yl)propyl]amino}phenyl)diazenyl]-4H-1,2,4-triazol-1-ium;

Salts of 1,4-diallyl-5-[(4-{methyl[3-(4-aza-1-azoniabicyclo[2.2.2]octan-1-yl)propyl]amino}phenyl)diazenyl]-4H-1,2,4-triazol-1-ium;

Salts of 1,4-diallyl-5-[(4-{ethyl[3-(4-aza-1-azoniabicyclo[2.2.2]octan-1-yl)propyl]amino}phenyl)diazenyl]-4H-1,2,4-triazol-1-ium;

Salts of 1,4-diallyl-5-[(4-{propyl[3-(4-aza-1-azoniabicyclo[2.2.2]octan-1-yl)propyl]amino}phenyl)diazenyl]-4H-1,2,4-triazol-1-ium;

Salts of 1,4-dibenzyl-5-[(4-{methyl[3-(4-aza-1-azoniabicyclo[2.2.2]octan-1-yl)propyl]amino}phenyl)diazenyl]-4H-1,2,4-triazol-1-ium;

Salts of 1,4-dibenzyl-5-[(4-{ethyl[3-(4-aza-1-azoniabicyclo[2.2.2]octan-1-yl)propyl]amino}phenyl)diazenyl]-4H-1,2,4-triazol-1-ium, and Salts of 1,4-dibenzyl-5-[(4-{propyl[3-(4-aza-1-azoniabicyclo[2.2.2]octan-1-yl)propyl]amino}phenyl)diazenyl]-4H-1,2,4-triazol-1-ium.

Within the first preferred embodiment, the following compounds are to be explicitly emphasized:

1,4-Dimethyl-5-[(4-{ethyl[2-(4-aza-1-azoniabicyclo[2.2.2]octan-1-yl)ethyl]amino}phenyl)diazenyl]-4H-1,2,4-triazol-1-ium dichloride;

1,4-Dimethyl-5-[(4-{ethyl[2-(4-aza-1-azoniabicyclo[2.2.2]octan-1-yl)ethyl]amino}phenyl)diazenyl]-4H-1,2,4-triazol-1-ium dibromide;

1,4-Dimethyl-5-[(4-{ethyl[2-(4-aza-1-azoniabicyclo[2.2.2]octan-1-yl)ethyl]amino}phenyl)diazenyl]-4H-1,2,4-triazol-1-ium bis-p-toluene sulfonate;

1,4-Dimethyl-5-[(4-{ethyl[2-(4-aza-1-azoniabicyclo[2.2.2]octan-1-yl)ethyl]amino}phenyl)diazenyl]-4H-1,2,4-triazol-1-ium sulfate;

1,4-Diethyl-5-[(4-{ethyl[2-(4-aza-1-azoniabicyclo[2.2.2]octan-1-yl)ethyl]amino}phenyl)diazenyl]-4H-1,2,4-triazol-1-ium dichloride;

1,4-Diethyl-5-[(4-{ethyl[2-(4-aza-1-azoniabicyclo[2.2.2]octan-1-yl)ethyl]amino}phenyl)diazenyl]-4H-1,2,4-triazol-1-ium dibromide;

1,4-Diethyl-5-[(4-{ethyl[2-(4-aza-1-azoniabicyclo[2.2.2]octan-1-yl)ethyl]amino}phenyl)diazenyl]-4H-1,2,4-triazol-1-ium bis-p-toluene sulfonate;

1,4-Diethyl-5-[(4-{ethyl[2-(4-aza-1-azoniabicyclo[2.2.2]octan-1-yl)ethyl]amino}phenyl)diazenyl]-4H-1,2,4-triazol-1-ium sulfate;

1,4-Diallyl-5-[(4-{ethyl[2-(4-aza-1-azoniabicyclo[2.2.2]octan-1-yl)ethyl]amino}phenyl)diazenyl]-4H-1,2,4-triazol-1-ium dichloride;

1,4-Diallyl-5-[(4-{ethyl[2-(4-aza-1-azoniabicyclo[2.2.2]octan-1-yl)ethyl]amino}phenyl)diazenyl]-4H-1,2,4-triazol-1-ium dibromide;

1,4-Diallyl-5-[(4-{ethyl[2-(4-aza-1-azoniabicyclo[2.2.2]octan-1-yl)ethyl]amino}phenyl)diazenyl]-4H-1,2,4-triazol-1-ium bis-p-toluene sulfonate, and 1,4-Diallyl-5-[(4-{ethyl[2-(4-aza-1-azoniabicyclo[2.2.2]octan-1-yl)ethyl]amino}phenyl)diazenyl]-4H-1,2,4-triazol-1-ium sulfate.

In the context of a second embodiment, it has also proven particularly significant for achieving the object if Y stands for =CH—.

Within this second embodiment, particularly preferred agents for dyeing and optionally simultaneously lightening keratinic fibers comprise a compound selected from the group of the:

Salts of 1,3-dimethyl-2-[(4-{methyl[2-(4-aza-1-azoniabicyclo[2.2.2]octan-1-yl)ethyl]amino}phenyl)diazenyl]-1H-imidazol-3-ium;

Salts of 1,3-dimethyl-2-[(4-{ethyl[2-(4-aza-1-azoniabicyclo[2.2.2]octan-1-yl)ethyl]amino}phenyl)diazenyl]-1H-imidazol-3-ium;

Salts of 1,3-dimethyl-2-[(4-{propyl[2-(4-aza-1-azoniabicyclo[2.2.2]octan-1-yl)ethyl]amino}phenyl)diazenyl]-1H-imidazol-3-ium;

Salts of 1,3-diethyl-2-[(4-{methyl[2-(4-aza-1-azoniabicyclo[2.2.2]octan-1-yl)ethyl]amino}phenyl)diazenyl]-1H-imidazol-3-ium;

Salts of 1,3-diethyl-2-[(4-{ethyl[2-(4-aza-1-azoniabicyclo[2.2.2]octan-1-yl)ethyl]amino}phenyl)diazenyl]-1H-imidazol-3-ium;

Salts of 1,3-diethyl-2-[(4-{propyl[2-(4-aza-1-azoniabicyclo[2.2.2]octan-1-yl)ethyl]amino}phenyl)diazenyl]-1H-imidazol-3-ium;

Salts of 1,3-diallyl-2-[(4-{methyl[2-(4-aza-1-azoniabicyclo[2.2.2]octan-1-yl)ethyl]amino}phenyl)diazenyl]-1H-imidazol-3-ium;

Salts of 1,3-diallyl-2-[(4-{ethyl[2-(4-aza-1-azoniabicyclo[2.2.2]octan-1-yl)ethyl]amino}phenyl)diazenyl]-1H-imidazol-3-ium;

Salts of 1,3-diallyl-2-[(4-{propyl[2-(4-aza-1-azoniabicyclo[2.2.2]octan-1-yl)ethyl]amino}phenyl)diazenyl]-1H-imidazol-3-ium;

Salts of 1,3-dibenzyl-2-[(4-{methyl[2-(4-aza-1-azoniabicyclo[2.2.2]octan-1-yl)ethyl]amino}phenyl)diazenyl]-1H-imidazol-3-ium;

Salts of 1,3-dibenzyl-2-[(4-{ethyl[2-(4-aza-1-azoniabicyclo[2.2.2]octan-1-yl)ethyl]amino}phenyl)diazenyl]-1H-imidazol-3-ium;

Salts of 1,3-dibenzyl-2-[(4-{propyl[2-(4-aza-1-azoniabicyclo[2.2.2]octan-1-yl)ethyl]amino}phenyl)diazenyl]-1H-imidazol-3-ium;

Salts of 1,3-dimethyl-2-[(2-methyl-4-{ethyl[2-(4-aza-1-azoniabicyclo[2.2.2]octan-1-yl)ethyl]amino}phenyl)diazenyl]-1H-imidazol-3-ium;

Salts of 1,3-dimethyl-2-[(2-methoxy-4-{ethyl[2-(4-aza-1-azoniabicyclo[2.2.2]octan-1-yl)ethyl]amino}phenyl)diazenyl]-1H-imidazol-3-ium;

Salts of 1,3-dimethyl-2-[(2-chlor-4-{ethyl[2-(4-aza-1-azoniabicyclo[2.2.2]octan-1-yl)ethyl]amino}phenyl)diazenyl]-1H-imidazol-3-ium;

Salts of 1,3-dimethyl-2-[(4-{methyl[3-(4-aza-1-azoniabicyclo[2.2.2]octan-1-yl)propyl]amino}phenyl)diazenyl]-1H-imidazol-3-ium;

Salts of 1,3-dimethyl-2-[(4-{ethyl[3-(4-aza-1-azoniabicyclo[2.2.2]octan-1-yl)propyl]amino}phenyl)diazenyl]-1H-imidazol-3-ium;

Salts of 1,3-dimethyl-2-[(4-{propyl[3-(4-aza-1-azoniabicyclo[2.2.2]octan-1-yl)propyl]amino}phenyl)diazenyl]-1H-imidazol-3-ium;

Salts of 1,3-diethyl-2-[(4-{methyl[3-(4-aza-1-azoniabicyclo[2.2.2]octan-1-yl)propyl]amino}phenyl)diazenyl]-1H-imidazol-3-ium;

Salts of 1,3-diethyl-2-[(4-{ethyl[3-(4-aza-1-azoniabicyclo[2.2.2]octan-1-yl)propyl]amino}phenyl)diazenyl]-1H-imidazol-3-ium;

Salts of 1,3-diethyl-2-[(4-{propyl[3-(4-aza-1-azoniabicyclo[2.2.2]octan-1-yl)propyl]amino}phenyl)diazenyl]-1H-imidazol-3-ium;

Salts of 1,3-diallyl-2-[(4-{methyl[3-(4-aza-1-azoniabicyclo[2.2.2]octan-1-yl)propyl]amino}phenyl)diazenyl]-1H-imidazol-3-ium;

Salts of 1,3-diallyl-2-[(4-{ethyl[3-(4-aza-1-azoniabicyclo[2.2.2]octan-1-yl)propyl]amino}phenyl)diazenyl]-1H-imidazol-3-ium;

Salts of 1,3-diallyl-2-[(4-{propyl[3-(4-aza-1-azoniabicyclo[2.2.2]octan-1-yl)propyl]amino}phenyl)diazenyl]-1H-imidazol-3-ium;

Salts of 1,3-dibenzyl-2-[(4-{methyl[3-(4-aza-1-azoniabicyclo[2.2.2]octan-1-yl)propyl]amino}phenyl)diazenyl]-1H-imidazol-3-ium;

Salts of 1,3-dibenzyl-2-[(4-{ethyl[3-(4-aza-1-azoniabicyclo[2.2.2]octan-1-yl)propyl]amino}phenyl)diazenyl]-1H-imidazol-3-ium, and Salts of 1,3-dibenzyl-2-[(4-{propyl[3-(4-aza-1-azoniabicyclo[2.2.2]octan-1-yl)propyl]amino}phenyl)diazenyl]-1H-imidazol-3-ium.

Among the compounds of the second embodiment which are again to be explicitly emphasized are the compounds selected from the group:

1,3-Dimethyl-2-[(4-{ethyl[2-(4-aza-1-azoniabicyclo[2.2.2]octan-1-yl)ethyl]amino}phenyl)diazenyl]-1H-imidazol-3-ium dichloride;

1,3-Dimethyl-2-[(4-{ethyl[2-(4-aza-1-azoniabicyclo[2.2.2]octan-1-yl)ethyl]amino}phenyl)diazenyl]-1H-imidazol-3-ium dibromide;

1,3-Dimethyl-2-[(4-{ethyl[2-(4-aza-1-azoniabicyclo[2.2.2]octan-1-yl)ethyl]amino}phenyl)diazenyl]-1H-imidazol-3-ium bis-p-toluene sulfonate, and 1,3-Dimethyl-2-[(4-{ethyl[2-(4-aza-1-azoniabicyclo[2.2.2]octan-1-yl)ethyl]amino}phenyl)diazenyl]-1H-imidazol-3-ium sulfate.

Further particularly preferred salts are explicitly listed further below in the disclosure of the compounds per se. Inventive agents that comprise the salts disclosed therein are likewise particularly preferred.

The inventive agents for dyeing and optionally simultaneously lightening keratinic fibers comprise the compound(s) of the Formula (I) in amounts above 1 ppm and less than 10 wt %, each relative to the total agent. Preferred inventive agents for dyeing and optionally simultaneously lightening keratinic fibers comprise the compound(s) of the Formula (I) in amounts of about 0.001 to about 5 wt %, for example about 0.0025 to about 2.5 wt %, for example about 0.005 to about 1.5 wt %, such as about 0.01 to about 1 wt %, each relative to the total agent.

The inventive agents are used for changing the color of keratinic fibers, especially human hair. The color change can result solely due to the cationic compound(s) of the Formula (I), although the inventive agents can also comprise additional further color changing substances, for example substantive dyes and/or oxidizing agents. Inventive agents for dyeing and optionally simultaneously lightening keratinic fibers which additionally comprise—based on their weight—0.001 to 5 wt % of one or more oxidation dye precursors and/or substantive dyes, are preferred in this regard.

The so-called oxidation dyes are used for long-lasting, intensive colorations with corresponding fastness characteristics. Such dyes usually comprise oxidation dye precursors, "developer components" and "coupler components". Under the influence of oxidizing agents or from atmospheric oxygen, the developer components form the actual colorants among each other or by coupling with one or more coupler components. Indeed, the oxidation dyes are characterized by excellent, long lasting coloration results. However, for colorations with a natural appearance, normally a mixture of a large number of oxidation dye precursors must be employed; in many cases, further substantive dyes are used for nuancing.

These additional chromphoric substances were described in detail in the priority document. Quite particularly preferred developer components are selected from at least one compound of the group formed from p-phenylenediamine, p-toluoylenediamine, 2-(β-hydroxyethyl)-p-phenylenediamine, 2-(α,β-dihydroxyethyl)-p-phenylenediamine, N,N-bis-(β-hydroxyethyl)-p-phenylenediamine, N-(4-amino-3-methylphenyl)-N-[3-(1H-imidazol-1-yl)propyl]amine, N,N'-bis-(β-hydroxyethyl)-N,N'-bis-(4-aminophenyl)-1,3-diaminopropan-2-ol, bis-(2-hydroxy-5-aminophenyl)-methane, 1,3-bis-(2,5-diaminophenoxy)-propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(α,β-dihydroxyethyl)-phenol and 4-amino-2-(diethylaminomethyl)-phenol, 4,5-diamino-1-(β-hydroxyethyl)-pyrazole, 2,4,5,6-tetraminopyrimidine, 4-hydroxy-2,5,6-triaminopyrimidine, 2-hydroxy-4,5,6-triaminopyrimidine, as well as the physiologically acceptable salts of these compounds.

Coupler components alone, in the context of the oxidative dyeing, do not form any significant coloration; rather they need the presence of developer components. Therefore it is inventively preferred that when using at least one developer component, at least one coupler component is also used.

Exemplary coupler components are selected from m-aminophenol, 5-amino-2-methylphenol, N-cyclopentyl-3-aminophenol, 3-amino-2-chloro-6-methylphenol, 2-hydroxy-4- aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol, 2,4-dichloro-3-aminophenol, 2-(2,4-diaminophenoxy)ethanol, 1,3-bis-(2,4-diaminophenoxy) propane, 1-methoxy-2-amino-4-(2-hydroxyethylamino) benzene, 1,3-bis-(2,4-diaminophenyl)propane, 2,6-bis-(2'-hydroxyethylamino)-1-methyl benzene, 2-({3-[(2-hydroxyethyl)amino]-4-methoxy-5-methylphenyl}amino) ethanol, 2-({3-[(2-hydroxyethyl)amino]-2-methoxy-5-methylphenyl}amino)ethanol, 2-({3-[(2-hydroxyethyl) amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, resorcinol monomethyl ether, 2-methylresorcinol, 5-methylresorcinol, 2,5-dimethylresorcinol, 2-chlororesorcinol, 4-chlororesorcinol, pyrogallol, 1,2,4-trihydroxybenzene, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 2,6-dihydroxy-3,4-dimethylpyridine, 3,4-diaminopyridine, 2-(2-methoxyethyl)amino-3-amino-6-methoxypyridine, 2-(4'-methoxyphenyl)amino-3-aminopyridine, 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, 2,3-dihydroxynaphthalene, 4-hydroxyindole, 6-hydroxyindole, 7-hydroxyindole, 4-hydroxyindoline, 6-hydroxyindoline, 7-hydroxyindoline, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine or mixtures of these compounds or their physiologically acceptable salts.

The coupler components are used in an amount of, for example, about 0.005 to about 20 wt %, such as, about 0.1 to about 5 wt %, in each case based on the ready-to-use oxidation dye.

Here, developer components and coupler components are generally used in approximately molar amounts relative to one another. Although the molar use has also proven to be expedient, a certain excess of individual oxidation dye precursors is not disadvantageous, meaning that developer components and coupler components may be present in a molar ratio of from about 1 to about 0.5 to about 1 to about 3, in particular, about 1 to about 1 to about 1 to about 2.

For temporary colorations, usually colorants or toners are used that comprise "substantives" as the coloring component. These are dye molecules that are directly absorbed onto the substrate and do not require any oxidative process to develop the color. These dyes include, for example, Henna that was already known in antiquity for dyeing skin and hair. In general, these colorations are significantly more sensitive to shampooing than are oxidative colorations, with the result that many unwanted nuance shifts or even a visible homogenous decolorization occur very much faster.

The inventive agents can further comprise a substantive dye. These are dyes that are directly absorbed onto the hair and do not require any oxidative process to develop the color.

Substantive dyes are usually nitrophenylenediamines, nitroaminophenols, azo dyes, anthraquinones or indophenols.

In an embodiment, the substantive dyes are each employed in quantities of about 0.001 to about 20 wt %, based on the total end-use preparation. The total amount of substantive dyes is for example about 20 wt % at most.

Substantive dyes can be sub-divided into anionic, cationic and non-ionic substantive dyes.

Exemplary substantive dyes are those known under the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, compounds known as Disperse Black 9, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)aminophenol, 2-(2-hydroxyethyl) amino-4,6-dinitrophenol, 4-[(2-hydroxyethyl)amino]-3-nitro-1-methyl benzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol. It is not required that each of the substantive dyestuffs be pure compounds. In fact, due to the manufacturing processes for the individual dyes, minor quantities of even more components may be comprised, in so far as they have no detrimental influence on the coloration result or that they must be excluded on other grounds, e.g. toxicological.

In addition, naturally occurring dyestuffs may also be added, as are comprised for example in henna red, henna neutral, henna black, camomile leaves, sandalwood, black tea, alder buckthorn bark, sage, logwood, madder root, cachou, cedar and alkanet root.

The inventive agents particularly additionally comprise hydrogen peroxide. Here, inventive agents for changing the color of keratinic fibers are particularly suitable which comprise about 0.5 to about 15 wt %, for example about 1 to about 12.5 wt %, for example about 2.5 to about 10 wt %, such as about 3 to about 6 wt % hydrogen peroxide (calculated as 100% concentrated $H_2O_2$).

The hydrogen peroxide can also be added in the form of its addition compounds on solid carriers, although the use of hydrogen peroxide itself is preferred. The hydrogen peroxide is added as a solution or in the form of a solid addition compound of hydrogen peroxide onto inorganic or organic compounds, such as, for example, sodium perborate, sodium percarbonate, magnesium percarbonate, sodium percarbamide, polyvinyl pyrrolidone.$nH_2O_2$ (n is a positive integer greater than 0), urea peroxide and melamine peroxide.

Aqueous hydrogen peroxide solutions are inventively quite particularly preferred. The concentration of a hydrogen peroxide solution is firstly determined from the statutory regulations and secondly according to the required effect; for example, about 6 to about 12 percentage solutions in water are used.

For a color change by means of lightening or bleaching of the substrate, for example the hair, then in addition to the oxidizing agents, in an embodiment a bleach booster is additionally added to the inventive cosmetic compositions.

Bleach boosters are added to increase the bleach effect of the oxidizing agent, especially of the hydrogen peroxide. Suitable bleach boosters are
(BV-i) compounds that under perhydrolysis conditions afford aliphatic peroxy carboxylic acids and/or optionally substituted perbenzoic acid, and/or
(BV-ii) salts of carbonates and/or salts of hydrogen carbonates, and/or
(BV-iii) organic carbonates, and/or
(BV-iv) carboxylic acids, and/or
(BV-v) peroxy compounds.

Bleach activators that can be used are compounds which, under perhydrolysis conditions, yield aliphatic peroxycarboxylic acids having preferably 1 to 10 carbon atoms, in particular 2 to 4 carbon atoms, and/or optionally substituted perbenzoic acid. Substances, which carry O-acyl and/or N-acyl groups of said number of carbon atoms and/or optionally substituted benzoyl groups, are suitable. Preference is given to polyacylated alkylenediamines, in particular tetraacetyl ethylenediamine (TAED), acylated triazine derivatives, in particular 1,5-diacetyl-2,4-dioxohexahydro-1,3,5-triazine (DADHT), acylated glycolurils, in particular tetraacetyl glycoluril (TAGU), N-acylimides, in particular N-nonanoyl succinimide (NOSI), acylated phenol sulfonates, in particular n-nonanoyl- or iso-nonanoyloxybenzene sulfonate (n- or iso-NOBS), carboxylic acid anhydrides, in particular phthalic anhydride, acylated polyhydric alcohols, in particular triacetin, ethylene glycol diacetate and 2,5-diacetoxy-2,5-dihydrofuran.

Exemplary carbonate or hydrogen carbonate salts are selected from a compound of the group consisting of the carbonate or hydrogen carbonate salts of ammonium, alkali metal (especially sodium and potassium), as well as alkaline earth metals (especially calcium). Particularly preferred carbonate or hydrogen carbonate salts are ammonium hydrogen carbonate, ammonium carbonate, sodium hydrogen carbonate, disodium carbonate, potassium hydrogen carbonate, dipotassium carbonate and calcium carbonate. These particularly preferred salts can be used as bleach boosters singly or in mixtures of at least two representatives.

Utilizable organic carbonates are selected from a compound of the group of the carbonic acid monoesters and/or from a compound of the group of the carbonic acid monoamides.

The compositions herein can comprise a compound selected from the group consisting of acetic acid, lactic acid, tartaric acid, citric acid, salicylic acid and ortho-phthalic acid, as the bleach boosting carboxylic acid.

In an embodiment, bleach boosters are peroxy compounds, especially inorganic peroxy compounds. The inventive bleach boosting peroxy compounds include neither hydrogen peroxide addition products with other components nor hydrogen peroxide itself. Moreover, the choice of peroxy compound is not limited. Suitable peroxy compounds are peroxy disulfate salts, persulfate salts, peroxy diphosphate salts (especially ammonium peroxy disulfate, potassium peroxy disulfate, sodium peroxy disulfate, ammonium persulfate, potassium persulfate, sodium persulfate, potassium peroxy diphosphate) and peroxides (such as barium peroxide and magnesium peroxide). Among these peroxide compounds that can also be added in combination, the peroxy disulfates, especially ammonium peroxy disulfate, are inventively preferred. Inventive agents for dyeing and optionally simultaneously lightening keratinic fibers are suitable here which additionally comprise about 0.01 to about 2 wt % of a solid peroxy compound, selected from ammonium, alkali metal and alkaline earth metal persulfates, peroxy monosulfates and peroxy disulfates, wherein preferred agents comprise peroxy disulfates that are, for example, selected from sodium peroxy disulfate and/or potassium peroxy disulfate and/or ammonium peroxy disulfate and wherein particularly suitable agents comprise at least two different peroxy disulfates.

Persulfates are also particularly suitable, especially the mixture of potassium peroxy sulfate, potassium hydrogen sulfate and potassium sulfate, known as Caro's salt.

The bleach boosters are comprised in the cosmetic compositions contemplated herein in amounts of about 5 to about 30% by weight, for example in amounts of about 8 to about 20% by weight, each based on the weight of the ready-for-use agent.

Furthermore, it has proven advantageous when the dye and lightening agents herein comprise non-ionic surface active substances.

In this regard, suitable surface active substances are those that have an HLB value of about 5.0 and above. For the definition of the HLB value, reference is expressly made to the explanations in Hugo Janistyn, Handbuch der Kosmetika und Riechstoffe, volume III: Die Körperpflegemittel, 2nd edition, Dr. Alfred Hüthig Verlag Heidelberg, 1973, pages 68-78 and Hugo Janistyn, Taschenbuch der modernen Parfümerie und Kosmetik, 4th edition, Wissenschaftliche Verlagsgesellschaft m.b.H. Stuttgart, 1974, pages 466-474, as well as the original works cited therein.

Exemplary non-ionic surface active substances are those that are commercially available as solids or liquids in pure form, due to their ease of processing. The definition of purity in this context does not refer to chemically pure compounds. In fact, particularly in the case of products from natural sources, mixtures of different homologs can be employed, for example with differing alkyl chain lengths, as are obtained in products based on natural fats and oils. Mixtures of different degrees of alkoxylation are also usually present in alkoxylated products. In this context the term purity refers rather to the fact that the chosen substances should preferably be free of solvents, diluents and other impurities.

The compositions contemplated herein can comprise as an additional ingredient an ammonium compound from the group ammonium chloride, ammonium carbonate, ammonium bicarbonate, ammonium sulfate and/or ammonium carbamate in an amount of about 0.5 to about 10, for example about 1 to about 5 wt %, relative to the total composition of the agent.

Furthermore, the inventive dyes and/or lighteners can comprise additional active substances, auxiliaries and additives, such as for example:
  non-ionic polymers, such as, for example, vinyl pyrrolidone/vinyl acrylate copolymers, polyvinyl pyrrolidone and vinyl pyrrolidone/vinyl acetate copolymers and polysiloxanes,
  cationic polymers such as quaternized cellulose ethers, polysiloxanes with quaternized groups, dimethyldiallylammonium chloride polymers, acrylamide-dimethyldiallylammonium chloride copolymers, diethyl sulfate-quaternized dimethylaminoethyl methacrylate-vinyl pyrrolidone copolymers, vinyl pyrrolidone-imidazolinium methochloride copolymers and quaternized polyvinyl alcohol,
  zwitterionic and amphoteric polymers, such as, for example, acrylamidopropyltrimethylammonium chloride/acrylate copolymers and octylacrylamide/methyl methacrylate/tert-butylaminoethyl methacrylate/2-hydroxypropyl methacrylate copolymers,
  anionic polymers, such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butylacrylamide terpolymers, thickeners like agar-agar, guar gum, alginates, xanthane gum, gum arabica, karaya gum, locust bean flour, linseed gums, dextrans, cellulose derivatives, e.g. methyl cellulose, hydroxyalkyl cellulose and carboxymethyl cellulose, starch fractions and derivatives of amylose, amylopectin and dextrins, clays such as e.g. bentonite or synthetic hydrocolloids such as e.g. polyvinyl alcohol, structurants such as maleic acid and lactic acid, hair conditioning compounds like phospholipids, for example soya lecithin, egg lecithin and cephalin, protein hydrolyzates, particularly those of elastin, collagen, keratin, milk protein, soya protein and wheat protein, their condensation products with fatty acids as well as quaternized protein hydrolyzates, perfume oils, dimethyl isosorbitol and cyclodextrins, solvents and solubilizers such as ethanol, isopropanol, ethylene glycol, propylene glycol, glycerin and diethylene glycol, fiber structure improvers, particularly mono, di and oligosaccharides, such as, for example glucose, galactose, fructose, fruit sugar and lactose, quaternized amines, such as methyl-1-alkylamidoethyl-2-alkylimidazolinium methosulfate, defoamers such as silicones, dyestuffs to color the composition, anti-dandruff active materials such as Piroctone Olamine, zinc Omadine and Climbazole, photo protective agents, in particular derivatized benzophenones, cinnamic acid derivatives and triazines, substances for adjusting the pH, such as, for example, customary acids, in particular food acids and bases, active substances, such as panthenol, pantothenic acid, allantoin, pyrrolidone carboxylic acids and salts thereof, and bisabolol, vitamins, provitamins and vitamin precursors, in particular those of groups A, $B_3$, $B_5$, $B_6$, C, E, F and H, plant extracts such as extracts from green tea, oak bark, stinging nettle, hamamelis, hops, camomile, burdock root, field horsetail, hawthorn, linden flowers, almonds, aloe vera, spruce needles, horse chestnut, sandal wood, juniper, coconut, mango, apricot, lime, wheat, kiwi, melon, orange, grapefruit, sage, rosemary, birch, malva, lady's smock, common yarrow, thyme, lemon balm, rest-harrow, coltsfoot, marshmallow (althaea), meristem, ginseng and ginger, cholesterol, texturizers such as sugar esters, polyol esters or polyol alkyl ethers, fats and waxes like spermaceti, beeswax, montan wax und paraffins, fatty alcohols and fatty acid esters, fatty acid alkanolamides, complexants such as EDTA, NTA, β-alanine diacetic acid and phosphonic acids, swelling and penetration substances such as glycerin, propylene glycol monoethyl ethers, carbonates, hydrogen carbonates, guanidines, ureas as well as primary, secondary and tertiary phosphates, opacifiers such as latex, styrene/PVP copolymers and styrene/acrylamide copolymers pearlizing compositions such as ethylene glycol mono- and distearate as well as PEG-3 distearate, pigments, stabilizers for hydrogen peroxide and other oxidizing agents, propellants such as propane-butane mixtures, $N_2O$, dimethyl ether, $CO_2$ and air, and antioxidants With regard to further optional ingredients and their amounts used, reference is expressly made to the relevant handbooks known to the person skilled in the art, for example the monograph by K. Schrader, Grundlagen und Rezepturen der Kosmetika, $2^{nd}$ edition, Hüthig Buch Verlag, Heidelberg, 1989.

The person skilled in the art will select these additional materials as a function of the desired properties of the agent.

The agents contemplated herein can comprise the ingredients in a suitable aqueous, alcoholic or aqueous-alcoholic carrier. For the purposes of dyeing the hair, such carriers are, for example, creams, emulsions, gels or also surfactant-containing foaming solutions, such as, for example, shampoos, foam aerosols or other preparations that are suitable for use on the hair. However, for storage, it is also possible to provide a formulation that is in powder form or even in tablet form, which is preferred for dyes and lighteners. For the purposes herein, aqueous-alcoholic solutions are understood as meaning aqueous solutions comprising about 3 to about 70% by weight of a $C_1$-$C_4$ alcohol, in particular, ethanol or isopropanol. The compositions contemplated herein can additionally comprise further organic solvents, such as, for example, methoxybutanol, benzyl alcohol, ethyl diglycol or 1,2-propylene glycol. Preference here is given to all water-soluble organic solvents.

In another exemplary embodiment, inventive agents additionally comprise a non-aqueous solvent, for example, wherein inventive agents comprise the solvent in a concentration of about 0.1 to about 30 wt %, for example in a concentration of about 1 to about 20 wt %, such as in a concentration of about 2 to about 10 wt %, each relative to the agent.

An exemplary solvent is selected from ethanol, n-propanol, isopropanol, n-butanol, propylene glycol, n-butylene glycol, glycerin, diethylene glycol monoethyl ether, diethylene glycol mono-n-butyl ether, phenoxyethanol and benzyl alcohol as well as their mixtures.

The pH of the inventive agent can be adjusted to a large degree by suitable ingredients such as acidifiers or alkalizers.

In principle, an oxidative coloration of the fibers can take place with atmospheric oxygen in the presence of oxidation dye precursors. However, it is preferred to use a chemical oxidizing agent, particularly when a lightening effect on human hair is desired in addition to the dyeing. This lightening effect may be desired independently of the dyeing method. The presence of oxidation dye precursors is therefore not a mandatory requirement for an addition of oxidizing agents into the inventive agents. Oxidizing agents that come under consideration are persulfates, chlorites and in particular hydrogen peroxide or its addition products onto urea, melamine as well as sodium borate.

In an embodiment, however, the oxidation dyeing composition is also applied to the hair together with a catalyst that activates the oxidation of the dye precursors, e.g., by atmospheric oxygen. Such catalysts are, for example, metal ions, iodides, quinones or certain enzymes.

Suitable metal ions are, for example, $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$, $Zn^{2+}$, $Cu^{2+}$ and $Mn^{2+}$. In principle, the metal ions can be employed in the form of any physiologically compatible salt or in the form of a complex compound. Preferred salts are the acetates, sulfates, halides, lactates and tartrates. By use of these metal salts, both the formation of the coloration can be accelerated, and the color tint can be selectively influenced.

Suitable enzymes are, for example, peroxidases, which can considerably enhance the effect of small amounts of hydrogen peroxide. Those enzymes that directly oxidize the oxidation dye precursors with the help of atmospheric oxygen are further inventively suitable, such as, for example, the laccases, or those which produce small amounts of hydrogen peroxide in situ and in so doing biocatalytically activate the oxidation of the dye precursors. Particularly suitable catalysts for the oxidation of the dye precursors are the so-called 2-electron oxidoreductases in combination with the substrates specific therefor, e.g., pyranose-oxidase and e.g. D-glucose or galactose, glucose-oxidase and D-glucose,
glycerin-oxidase and glycerin,
pyruvate-oxidase and pyruvic acid or its salts,
alcohol-oxidase and alcohol (MeOH, EtOH),
lactate-oxidase and lactic acid or its salts,
tyrosinase-oxidase and tyrosin,
uricase and uric acid or its salts,
choline oxidase and choline,
amino acid oxidase and amino acids.

When using oxidizing agents, the actual dyeing composition is expediently prepared directly prior to use by mixing the preparation of the oxidizing agent with the preparation comprising the compounds of the Formula (I) and optionally dye precursors. In an embodiment, the resulting ready-for-use hair coloration preparation has a pH in the range of from about 6 to about 12. In another embodiment, the hair dye is applied in a weakly alkaline milieu. The application temperatures can be in a range of from about 15 to about 40° C. After a contact time of from about 5 to about 45 minutes, the hair dye is removed from the hair by rinsing. There is no need to wash the hair with a shampoo afterwards if a strong surfactant-containing carrier, e.g. a color enhancing shampoo, was used.

Particularly in the case of hair which is difficult to dye, it is possible to apply a composition contemplated herein to the hair optionally with additional dye precursors but also without prior mixing with the oxidizing component. After an application time of from about 20 to about 30 minutes, and optionally after an intermediate rinse, the oxidation component is applied. After an application time of from about 10 to about 20 minutes, the hair is then rinsed and if desired shampooed. In this embodiment, according to a first variant, in which the prior application of the dye precursors was intended to afford a better penetration into the hair, the agent is adjusted to a pH of about 4 to about 7. According to a second variant, initially an air oxidation is aimed for, wherein the applied agent has a pH for example of from about 7 to about 10. In the subsequent accelerated post-oxidation, the use of acidically adjusted peroxydisulfate solutions can be suitable as the oxidizing agent.

For the application of the inventive agent on the hair, the dye and/or lightener are blended with a hydrogen peroxide solution immediately prior to the application. The concentration of this hydrogen peroxide solution is firstly determined from the statutory regulations and secondly according to the required effect; generally about 6 to about 12 percent solutions in water are used. The weight ratios of dye and/or lightener and hydrogen peroxide solution are usually in the range of from about 1:1 to about 1:2, wherein an excess of hydrogen peroxide solution would be chosen when a not too pronounced bleaching effect is wanted.

The inventive agents can further comprise additional ingredients. An addition of certain metal ions or metal complexes for example can be suitable in order to obtain intensive colorations. In this regard, inventive agents can be used that additionally comprise Cu, Fe, Mn, Ru ions or complexes of these ions.

In another embodiment, inventive agents for dyeing and optionally simultaneously lightening keratinic fibers additionally comprise Cu, Fe, Mn, Co, Ce, V, Ru ions or complexes of these ions, wherein suitable agents comprise about 0.0001 to about 2.5 wt %, for example from about 0.001 to about 1 wt % of a compound of the group copper chloride ($CuCl_2$), copper sulfate ($CuSO_4$), iron (II) sulfate, manganese (II) sulfate, manganese (II) chloride, cobalt (II) chloride, cerium sulfate, cerium chloride, vanadium sulfate, manganese dioxide ($MnO_2$).

In another embodiment, so-called complexants are also added. Complexants are substances that can complex metal ions. Suitable complexants are so-called chelating agents, i.e. substances that form cyclic compounds with metal ions, wherein a single ligand occupies more than one coordination site on a central atom, i.e. is at least bidentate. Thus in this case, compounds that are normally linear are ring-closed by complex formation with an ion. The number of the bonded ligands depends on the coordination number of the central ion.

Suitable and—in the context herein—preferred chelating agents are, for example polyoxycarboxylic acids, polyamines, ethylenediaminetetraacetic acid (EDTA) and nitrilotriacetic acid (NTA) and hydroxyethane diphosphonic acids and their alkali metal salts. Complexing polymers, i.e., polymers which, either in the main chain itself or laterally thereof, carry functional groups that are capable of acting as ligands and which react with suitable metal atoms, generally to form chelate complexes, may also be used herein. In this regard, the polymer-bound ligands of the resulting metal complexes can originate from one macromolecule or even from various polymer chains. The latter crosslink the material, in so far as the complexing polymers were not already crosslinked through covalent bonds.

Complexing groups (ligands) of usual complexing polymers are iminoacetic acid, hydroxyquinoline, thiourea, guanidine, dithiocarbamate, hydroxamic acid, amidoxime, amino phosphoric acid, (cycl.) polyamino, mercapto, 1,3-dicarbonyl and crown ether groups with sometimes very selective activities towards ions of different metals. Base polymers of many even commercially important complexing polymers are polystyrene, polyacrylates, polyacrylonitrile, polyvinyl alcohols, polyvinylpyridines and polyethylene imines. Natural polymers such as cellulose, starch or chitin are also complexing polymers. Moreover, they can be provided with additional ligand functionality by polymer-analogous conversions.

In the context herein, it is suitable to employ one or more chelating complexants from the groups of the:
(i) polycarboxylic acids where the sum of carboxyl and optionally hydroxyl groups is at least 5,
(ii) nitrogen-containing mono- or polycarboxylic acids,
(iii) geminal diphosphonic acids,
(iv) amino phosphonic acids,
(v) phosphono polycarboxylic acids, and
(vi) cyclodextrins.

Exemplary agents comprise one or more substances from the group including:
(a) nitrilotriacetic acid (NTA),
(b) diethylenetriaminepentaacetic acid (DTPA),
(c) ethylenediaminedisuccinic acid (EDDS),
(d) ethylenediamineglutaric acid (EDGA),
(e) 2-hydroxypropylenediaminedisuccinic acid (HPDS), (f) glycinamide-N,N'-disuccinic acid (GADS),
(g) ethylenediamine-N—N'-diglutaric acid (EDDG),
(h) 2-hydroxypropylenediamine-N—N'-disuccinic acid (HP-DDS),
(i) ethylenediaminetetraacetic acid (EDTA),
(j) ethylenedicysteinic acid (EDC),
(k) diaminoalkyldi(sulfosuccinic acid) (DDS),
(l) ethylenediamine-N—N'-bis(ortho-hydroxyphenylacetic acid) (EDDHA),
(m) N-2-hydroxyethyl-N,N-diacetic acid,
(n) glycerylimino diacetic acid,
(o) imino diacetic acid-N-2-hydroxypropyl sulfonic acid
(p) aspartic acid-N-carboxymethyl-N-2,5-hydroxypropyl-3-sulfonic acid,
(q) ß-alanine-N,N'-diacetic acid,
(r) aspartic acid-N,N'-diacetic acid
(s) aspartic acid-N-monoacetic acid, and
(t) dipicolinic acid,
(u) as well as their salts and/or derivatives.

In the context herein, some representatives from the above-mentioned substance groups are particularly suitable. Inventively particularly suitable agents for dyeing and optionally simultaneously lightening keratinic fibers additionally comprise one or more chelating complexants from the group of the:
(i) polycarboxylic acids where the sum of carboxyl and optionally hydroxyl groups is at least 5,
(ii) nitrogen-containing mono- or polycarboxylic acids,
(iii) geminal diphosphonic acids,
(iv) amino phosphonic acids,
(v) phosphono polycarboxylic acids, and
(vi) cyclodextrins,
wherein exemplary agents comprise phosphonates, for example hydroxyalkane or aminoalkane phosphonates and for example 1,1-hydroxyethane-1,1-diphosphonate (HEDP) or its di- or tetrasodium salt and/or ethylenediaminetetramethylene phosphonate (EDTMP) or its hexasodium salt and/or diethylenetriaminepentamethylene phosphonate (DTPMP) or its hepta or octasodium salt.

Exemplary agents are formulated to be water-poor or anhydrous. Such agents comprise less than about 5 wt %, for example less than about 2 wt %, for example less than about 1 wt %, such as less than about 0.5 wt % water, wherein suitable agents are anhydrous. The water content of the agent can be determined by Karl Fischer titration, for example.

A second embodiment is a method for dyeing and optionally simultaneously lightening keratinic fibers, especially human hair, in which
if desired, a pre-treatment agent M1 is deposited onto the fibers, then
an agent M2 is used on the fibers, wherein if desired an additional agent M3 is added to the agent M2 prior to the application,
this agent M2 is rinsed out of the fibers after about 5 to about 30 minutes and after the treatment, a post-treatment agent M4 is optionally applied onto the fibers
and is once more rinsed out after a dwell time of some minutes,
wherein at least one of the agents M1, M2 or M3 is an inventive agent.

Consequently, the inventive agents can be formulated as a one component agent (dye and lightener M2 or post-treatment agent M4), as a two component agent (M2+M3) or as a three component agent (M2+M3+M4) and used appropriately. A segregation in multi-component systems lends itself in particular in cases where incompatibilities of the ingredients are expected or suspected; in such systems the agent to be added is prepared by the consumer by blending the components directly prior to the application.

In an exemplary embodiment, a dyeing and lightening method provides that the lightening cream and the oxidizing agent are initially separated in this regard. A further embodiment is consequently a method for dyeing and lightening human hair, in which method an aqueous-based composition, comprising hydrogen peroxide, is blended with an inventive agent to form a homogenous composition, and this is applied onto the hair.

In exemplary inventive methods of this type, the aqueous-based composition comprises, based on its weight, about 1 to about 20 wt %, for example about 2 to about 10 wt %, such as about 3 to about 6 wt % hydrogen peroxide, calculated as 100% conc. $H_2O_2$.

In another exemplary method of this type, the aqueous-based composition comprising hydrogen peroxide is blended with an inventive agent in the weight ratio of from about 1:5 to about 10:1, for example about 1:2 to about 5:1, such as about 1:2 to about 2:1 to form a homogenous composition, and this is applied onto the hair.

Alternatively, as mentioned above, a three component system can also be applied. A further exemplary embodiment is consequently a method for dyeing and lightening human hair, in which method an aqueous-based composition, comprising hydrogen peroxide, is blended with another agent that suitably comprises an alkalizer and/or substantive hair dye and/or an oxidation dye precursor, and an inventive agent to form a homogenous composition, and this is applied onto the hair.

With reference to further embodiments of the method contemplated herein, the statement made concerning the agents contemplated herein applies mutatis mutandis.

The dyeing is particularly supported by physical measures. Inventive methods, in which the application is supported by the action of heat, IR and/or UV radiation during the contact time, are suitable embodiments contemplated herein.

The compounds of the general Formula (I) are very well suited as substantives for hair dyeing. In dyeing, extremely intensive color nuances with very good fastness characteristics are obtained, especially in the yellow, orange and red zone. The substantives, with the simultaneous application of oxidizing agents such as hydrogen peroxide or a mixture of hydrogen peroxide and peroxide disulfates, likewise afford lightened nuances without weakening color intensity and color brilliance. In this way the simultaneous lightening and dyeing of hair becomes possible, in that a lightened coloration can be achieved even on dark hair.

A further exemplary embodiment is consequently the use of dicationic azo dyes of the Formula (I):

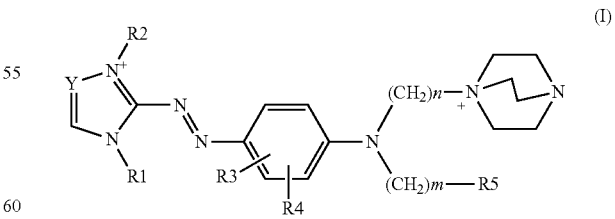

in which
Y stands either for =CH— or a nitrogen atom,
$R^1$, $R^2$ stand independently of one another for a $C_1$-$C_6$ alkyl group, a $C_2$-$C_6$ alkenyl group, a hydroxy $C_1$-$C_6$ alkyl group, a polyhydroxy $C_2$-$C_6$ alkyl group, a $C_1$-$C_6$ alkoxy $C_2$-$C_6$ alkyl group, a cyano $C_1$-$C_6$ alkyl group, an aryl group or an aryl $C_1$-$C_6$ alkyl group, $R^3$, $R^4$ stand independently of one another for a hydrogen atom, a $C_1$-$C_6$ alkyl group, a halogen atom (fluorine, chlorine, bromine or iodine), a $C_1$-$C_6$ alkoxy group, an amino group, a $C_1$-$C_6$ alkylamino group, a di-$C_1$-$C_6$ alkylamino group, a hydroxyl group or that $R^3$ and $R^4$ together form a 5-, 6- or 7-membered, saturated or unsaturated ring that can optionally comprise additional heteroatoms or can carry additional substituents, n, m stand independently of one another for a whole number from 1 to 6, $R^5$ stands for a hydrogen atom, a $C_1$-$C_6$ alkoxy group, a halogen atom (fluorine, chlorine, bromine or iodine), a hydroxyl group, a $C_1$-$C_6$ alkoxy $C_2$-$C_6$ alkyloxy group, a nitrile group, an aryl group or a heteroaryl group, $X^-$ stands for a monovalent anion, preferably for halide, hydrogen sulfate, ½ sulfate, benzene sulfonate, p-toluene sulfonate, acetate, citrate, lactate, tetrafluoroborate, trifluoromethane sulfonate, hexafluorophosphate.

The compounds are suitably added in order to achieve certain advantageous effects. Suitable uses are to:

increase the fastness properties of the colorations and/or
increase the color brilliance and/or
increase the skin compatibility of dyeing agents or lighteners.

With reference to further exemplary uses, the statement made concerning the preferred agents is correspondingly valid.

The cationic compounds that are comprised in the inventive agents are previously unknown. A further embodiment is consequently dicationic azo dyes of the Formula (I):

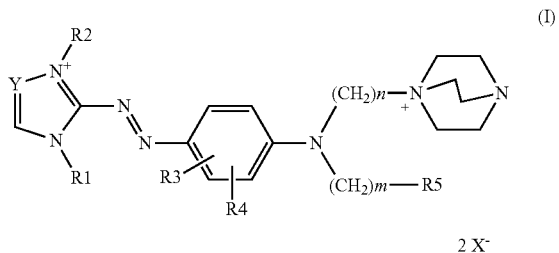

(I)

2 X⁻ in which

Y stands either for =CH— or a nitrogen atom, $R^1$, $R^2$ stand independently of one another for a $C_1$-$C_6$ alkyl group, a $C_2$-$C_6$ alkenyl group, a hydroxy $C_1$-$C_6$ alkyl group, a polyhydroxy $C_2$-$C_6$ alkyl group, a $C_1$-$C_6$ alkoxy $C_2$-$C_6$ alkyl group, a cyano $C_1$-$C_6$ alkyl group, an aryl group or an aryl $C_1$-$C_6$ alkyl group, $R^3$, $R^4$ stand independently of one another for a hydrogen atom, a $C_1$-$C_6$ alkyl group, a halogen atom (fluorine, chlorine, bromine or iodine), a $C_1$-$C_6$ alkoxy group, an amino group, a $C_1$-$C_6$ alkylamino group, a di-$C_1$-$C_6$ alkylamino group, a hydroxyl group or that $R^3$ and $R^4$ together form a 5-, 6- or 7-membered, saturated or unsaturated ring that can optionally comprise additional heteroatoms or can carry additional substituents, n, m stand independently of one another for a whole number from 1 to 6, $R^5$ stands for a hydrogen atom, a $C_1$-$C_6$ alkoxy group, a halogen atom (fluorine, chlorine, bromine or iodine), a hydroxyl group, a $C_1$-$C_6$ alkoxy $C_2$-$C_6$ alkyloxy group, a nitrile group, an aryl group or a heteroaryl group, $X^-$ stands for a monovalent anion, preferably for halide, hydrogen sulfate, ½ sulfate, benzene sulfonate, p-toluene sulfonate, acetate, citrate, lactate, tetrafluoroborate, trifluoromethane sulfonate, hexafluorophosphate.

Exemplary cationic derivatives suitable for use herein are selected from:

Salts of 1,4-dimethyl-5-[(4-{methyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(4-{propyl[2-(4-aza-1-azoniabicyclo[2.2.2]octan-1-yl)ethyl]amino}phenyl)diazenyl]-4H-1,2,4-triazol-1-ium;

Salts of 1,4-diethyl-5-[(4-{methyl[2-(4-aza-1-azoniabicyclo[2.2.2]octan-1-yl)ethyl]amino}phenyl)diazenyl]-4H-1,2,4-triazol-1-ium;

Salts of 1,4-diethyl-5-[(4-{ethyl[2-(4-aza-1-azoniabicyclo[2.2.2]octan-1-yl)ethyl]amino}phenyl)diazenyl]-4H-1,2,4-triazol-1-ium;

Salts of 1,4-diethyl-5-[(4-{propyl[2-(4-aza-1-azoniabicyclo[2.2.2]octan-1-yl)ethyl]amino}phenyl)diazenyl]-4H-1,2,4-triazol-1-ium;

Salts of 1,4-diallyl-5-[(4-{methyl[2-(4-aza-1-azoniabicyclo[2.2.2]octan-1-yl)ethyl]amino}phenyl)diazenyl]-4H-1,2,4-triazol-1-ium;

Salts of 1,4-diallyl-5-[(4-{ethyl[2-(4-aza-1-azoniabicyclo[2.2.2]octan-1-yl)ethyl]amino}phenyl)diazenyl]-4H-1,2,4-triazol-1-ium;

Salts of 1,4-diallyl-5-[(4-{propyl[2-(4-aza-1-azoniabicyclo[2.2.2]octan-1-yl)ethyl]amino}phenyl)diazenyl]-4H-1,2,4-triazol-1-ium;

Salts of 1,4-dibenzyl-5-[(4-{methyl[2-(4-aza-1-azoniabicyclo[2.2.2]octan-1-yl)ethyl]amino}phenyl)diazenyl]-4H-1,2,4-triazol-1-ium;

Salts of 1,4-dibenzyl-5-[(4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dibenzyl-5-[(4-{propyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(2-methyl-4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(2-methoxy-4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(2-chlor-4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(4-{methyl[3-(4-aza-1-azoniabicyclo[2.2.2]octan-1-yl)propyl]amino}phenyl)diazenyl]-4H-1,2,4-triazol-1-ium;

Salts of 1,4-dimethyl-5-[(4-{ethyl[3-(4-aza-1-azoniabicyclo[2.2.2]octan-1-yl)propyl]amino}phenyl)diazenyl]-4H-1,2,4-triazol-1-ium;

Salts of 1,4-dimethyl-5-[(4-{propyl[3-(4-aza-1-azoniabicyclo[2.2.2]octan-1-yl)propyl]amino}phenyl)diazenyl]-4H-1,2,4-triazol-1-ium;

Salts of 1,4-diethyl-5-[(4-{methyl[3-(4-aza-1-azoniabicyclo[2.2.2]octan-1-yl)propyl]amino}phenyl)diazenyl]-4H-1,2,4-triazol-1-ium;

Salts of 1,4-diethyl-5-[(4-{ethyl[3-(4-aza-1-azoniabicyclo[2.2.2]octan-1-yl)propyl]amino}phenyl)diazenyl]-4H-1,2,4-triazol-1-ium;
Salts of 1,4-diethyl-5-[(4-{propyl[3-(4-aza-1-azoniabicyclo[2.2.2]octan-yl)propyl]amino}phenyl)diazenyl]-4H-1,2,4-triazol-1-ium;
Salts of 1,4-diallyl-5-[(4-{methyl[3-(4-aza-1-azoniabicyclo[2.2.2]octan-yl)propyl]amino}phenyl)diazenyl]-4H-1,2,4-triazol-1-ium;
Salts of 1,4-diallyl-5-[(4-{ethyl[3-(4-aza-1-azoniabicyclo[2.2.2]octan-yl)propyl]amino}phenyl)diazenyl]-4H-1,2,4-triazol-1-ium;
Salts of 1,4-diallyl-5-[(4-{propyl[3-(4-aza-1-azoniabicyclo[2.2.2]octan-yl)propyl]amino}phenyl)diazenyl]-4H-1,2,4-triazol-1-ium;
Salts of 1,4-dibenzyl-5-[(4-{methyl[3-(4-aza-1-azoniabicyclo[2.2.2]octan-yl)propyl]amino}phenyl)diazenyl]-4H-1,2,4-triazol-1-ium;
Salts of 1,4-dibenzyl-5-[(4-{ethyl[3-(4-aza-1-azoniabicyclo[2.2.2]octan-yl)propyl]amino}phenyl)diazenyl]-4H-1,2,4-triazol-1-ium;
Salts of 1,4-dibenzyl-5-[(4-{propyl[3-(4-aza-1-azoniabicyclo[2.2.2]octan-yl)propyl]amino}phenyl)diazenyl]-4H-1,2,4-triazol-1-ium;
Salts of 1,3-dimethyl-2-[(4-{methyl[2-(4-aza-1-azoniabicyclo[2.2.2]octan-yl)ethyl]amino}phenyl)diazenyl]-1H-imidazol-3-ium;
Salts of 1,3-dimethyl-2-[(4-{ethyl[2-(4-aza-1-azoniabicyclo[2.2.2]octan-yl)ethyl]amino}phenyl)diazenyl]-1H-imidazol-3-ium;
Salts of 1,3-dimethyl-2-[(4-{propyl[2-(4-aza-1-azoniabicyclo[2.2.2]octan-yl)ethyl]amino}phenyl)diazenyl]-1H-imidazol-3-ium;
Salts of 1,3-diethyl-2-[(4-{methyl[2-(4-aza-1-azoniabicyclo[2.2.2]octan-yl)ethyl]amino}phenyl)diazenyl]-1H-imidazol-3-ium;
Salts of 1,3-diethyl-2-[(4-{ethyl[2-(4-aza-1-azoniabicyclo[2.2.2]octan-yl)ethyl]amino}phenyl)diazenyl]-1H-imidazol-3-ium;
Salts of 1,3-diethyl-2-[(4-{propyl[2-(4-aza-1-azoniabicyclo[2.2.2]octan-yl)ethyl]amino}phenyl)diazenyl]-1H-imidazol-3-ium;
Salts of 1,3-diallyl-2-[(4-{methyl[2-(4-aza-1-azoniabicyclo[2.2.2]octan-yl)ethyl]amino}phenyl)diazenyl]-1H-imidazol-3-ium;
Salts of 1,3-diallyl-2-[(4-{ethyl[2-(4-aza-1-azoniabicyclo[2.2.2]octan-yl)ethyl]amino}phenyl)diazenyl]-1H-imidazol-3-ium;
Salts of 1,3-diallyl-2-[(4-{propyl[2-(4-aza-1-azoniabicyclo[2.2.2]octan-yl)ethyl]amino}phenyl)diazenyl]-1H-imidazol-3-ium;
Salts of 1,3-dibenzyl-2-[(4-{methyl[2-(4-aza-1-azoniabicyclo[2.2.2]octan-yl)ethyl]amino}phenyl)diazenyl]-1H-imidazol-3-ium;
Salts of 1,3-dibenzyl-2-[(4-{ethyl[2-(4-aza-1-azoniabicyclo[2.2.2]octan-yl)ethyl]amino}phenyl)diazenyl]-1H-imidazol-3-ium;
Salts of 1,3-dibenzyl-2-[(4-{propyl[2-(4-aza-1-azoniabicyclo[2.2.2]octan-yl)ethyl]amino}phenyl)diazenyl]-1H-imidazol-3-ium;
Salts of 1,3-dimethyl-2-[(2-methyl-4-{ethyl[2-(4-aza-1-azoniabicyclo[2.2.2]octan-1-yl)ethyl]amino}phenyl)diazenyl]-1H-imidazol-3-ium;
Salts of 1,3-dimethyl-2-[(2-methoxy-4-{ethyl[2-(4-aza-1-azoniabicyclo[2.2.2]octan-1-yl)ethyl]amino}phenyl)diazenyl]-1H-imidazol-3-ium;
Salts of 1,3-dimethyl-2-[(2-chlor-4-{ethyl[2-(4-aza-1-azoniabicyclo[2.2.2]octan-1-yl)ethyl]amino}phenyl)diazenyl]-1H-imidazol-3-ium;
Salts of 1,3-dimethyl-2-[(4-{methyl[3-(4-aza-1-azoniabicyclo[2.2.2]octan-1-yl)propyl]amino}phenyl)diazenyl]-1H-imidazol-3-ium;
Salts of 1,3-dimethyl-2-[(4-{ethyl[3-(4-aza-1-azoniabicyclo[2.2.2]octan-1-yl)propyl]amino}phenyl)diazenyl]-1H-imidazol-3-ium;
Salts of 1,3-dimethyl-2-[(4-{propyl[3-(4-aza-1-azoniabicyclo[2.2.2]octan-1-yl)propyl]amino}phenyl)diazenyl]-1H-imidazol-3-ium;
Salts of 1,3-diethyl-2-[(4-{methyl[3-(4-aza-1-azoniabicyclo[2.2.2]octan-1-yl)propyl]amino}phenyl)diazenyl]-1H-imidazol-3-ium;
Salts of 1,3-diethyl-2-[(4-{ethyl[3-(4-aza-1-azoniabicyclo[2.2.2]octan-1-yl)propyl]amino}phenyl)diazenyl]-1H-imidazol-3-ium;
Salts of 1,3-diethyl-2-[(4-{propyl[3-(4-aza-1-azoniabicyclo[2.2.2]octan-1-yl)propyl]amino}phenyl)diazenyl]-1H-imidazol-3-ium;
Salts of 1,3-diallyl-2-[(4-{methyl[3-(4-aza-1-azoniabicyclo[2.2.2]octan-1-yl)propyl]amino}phenyl)diazenyl]-1H-imidazol-3-ium;
Salts of 1,3-diallyl-2-[(4-{ethyl[3-(4-aza-1-azoniabicyclo[2.2.2]octan-1-yl)propyl]amino}phenyl)diazenyl]-1H-imidazol-3-ium;
Salts of 1,3-diallyl-2-[(4-{propyl[3-(4-aza-1-azoniabicyclo[2.2.2]octan-1-yl)propyl]amino}phenyl)diazenyl]-1H-imidazol-3-ium;
Salts of 1,3-dibenzyl-2-[(4-{methyl[3-(4-aza-1-azoniabicyclo[2.2.2]octan-1-yl)propyl]amino}phenyl)diazenyl]-1H-imidazol-3-ium;
Salts of 1,3-dibenzyl-2-[(4-{ethyl[3-(4-aza-1-azoniabicyclo[2.2.2]octan-1-yl)propyl]amino}phenyl)diazenyl]-1H-imidazol-3-ium, and
Salts of 1,3-dibenzyl-2-[(4-{propyl[3-(4-aza-1-azoniabicyclo[2.2.2]octan-1-yl)propyl]amino}phenyl)diazenyl]-1H-imidazol-3-ium;

EXAMPLES

The synthesis of 1,4-dimethyl-5-[(4-{ethyl[2-(4-aza-1-azoniabicyclo-[2.2.2]octan-1-yl)ethyl]amino}phenyl)diazenyl]-4H-1,2,4-triazol-1-ium bis-p-toluene sulfonate (DZ1) and of 1-[2-(N-ethyl-N-phenylamino)ethyl]-4-aza-1-azoniabicyclo[2.2.2]octane, chloride was described in detail in the priority document.

The following coloring creams were produced:

| | |
|---|---|
| Hydrenol ® D | 6.0 g |
| Lorol ® (techn.) | 6.0 g |
| Eumulgin ® RH 40 | 1.0 g |
| Eumulgin ® B1 | 3.0 g |
| Eumulgin ® B2 | 3.0 g |
| PHB methyl ester | 0.3 g |
| PHB-propyl ester | 0.2 g |
| Phenoxyethanol | 1.0 g |
| Polydiol ® 400 | 5.0 g |
| Substantive | 1.0 g |
| Ammonium sulfate | 1.0 g (in 30.0 g water) |
| Natrosol ® 250 HR | 1.0 g (in 15.0 g water) |
| NaOH | 0.1% pH adjustment |
| water | ad 100 g |

The first nine components were melted together at 80° C. and the dye was then added. This mixture was emulsified with a solution of the ammonium sulfate in 30 g water. 1.0 g Natrosol® 250 HR in 15.0 g water was then to be added for swelling. The pH listed in Table 2 was adjusted with 0.1% caustic soda, and water was then added to make up 100 g.

1.1.2 Cationic Coloring Cream

| | |
|---|---|
| Stenol® 16/18 | 4.0 g |
| Eumulgin® B1 | 1.0 g |
| Dehyquart® A-CA | 2.0 g |
| Ammonium sulfate | 1.0 g (in 30.0 g water) |
| Substantive | 1.0 g |
| Water | ad 100 g |

The Stenol® 16/18 was melted together with Eumulgin® B1 and Dehyquart® A-CA, and the melt was then emulsified with hot water. The dye and the aqueous ammonium sulfate solution were then added. The pH was adjusted with ammonia or citric acid to the value listed in Table 2, and water was then added to make up 100 g.

1.1.3 Anionic Coloring Cream

| | |
|---|---|
| Hydrenol® D | 1.0 g |
| Lorol® techn. | 1.0 g |
| Akypo Soft® RLM 45N | 1.1 g |
| PHB propyl ester | 0.1 g |
| PHB methyl ester | 0.1 g |
| Ammonium sulfate | 1.0 g (in 30.0 g water) |
| Substantive DZ | 1.0 g |
| Water | ad 100 g |

The first five components were melted together. This melt was emulsified with hot water and then the dye, pre-dissolved or pre-dispersed in water, and the ammonium sulfate solution were added. The pH was adjusted with ammonia or citric acid to the value listed in the Table, and water was then added to make up 100 g.

1.2 Index of the Added Raw Materials

Akypo RLM 45 NV® Lauryl alcohol-4.5-EO-acetic acid sodium salt (min. 22% active substance content); INCI name: Sodium Laureth-5 Carboxylate) (Chem-Y)

Dehyquart® A-CA Trimethylhexadecylammonium chloride (ca. 24-26% active substance; INCI name: Aqua (Water), Cetrimonium Chloride) (Cognis)

Eumulgin® B1 Cetylstearyl alcohol with ca. 12-EO-units (INCI name: Ceteareth-12) (Cognis)

Eumulgin® B2 Cetylstearyl alcohol with ca. 20 EO-units (INCI name: Ceteareth-20) (Cognis)

Eumulgin® RH 40 hydrogenated castor oil with ca. 40 EO units (INCI name: PEG-40 Hydrogenated Castor Oil) (Cognis)

Hydrenol® D $C_{16-18}$ Fatty alcohol (INCI name: Cetearyl alcohol) (Cognis)

Lorol (Techn.)® $C_{12-18}$ Fatty alcohol (INCI name: Coconut Alcohol (Cognis)

Natrosol® 250 HR Hydroxyethyl cellulose (INCI name: Hydroxyethylcellulose) (Hercules)

Polydiol® 400 Polyethylene glycol (INCI name: PEG-8) (Cognis)

Stenol® 1618 $C_{16-18}$ Fatty alcohol (INCI name: Cetearyl alcohol) (Cognis)

1.3 Dyeing 1.8 g of each of the coloring creams were applied onto a ca. 6 cm long strand of human hair (Kerling Euronaturhaar, blonde) and left for 30 minutes at 30° C. At the end of the contact time the hair was rinsed out, washed with a conventional hair shampoo and then dried. The hair strands were then dyed in the nuances listed in the following Tables.

DZ1: 1,4-Dimethyl-5-[(4-{ethyl[2-(4-aza-1-azoniabicyclo-[2.2.2]octan-1-yl)ethyl]-amino}phenyl)diazenyl]-4H-1,2,4-triazol-1-ium bis-p-toluene sulfonate

| Dye | Coloring Cream | pH | Color shade (intensity) |
|---|---|---|---|
| DZ1 | 1 | 7.0 | strawberry red (+++) |
| DZ1 | 1 | 9.0 | blood red (+++) |
| DZ1 | 2 | 7.0 | strawberry red (+++) |
| DZ1 | 2 | 9.0 | blood red (+++) |
| DZ1 | 3 | 7.0 | strawberry red (+++) |
| DZ1 | 3 | 9.0 | blood red (+++) |

Intensity: + = low ++ = medium +++ = high 2.4 Determination of the Oxidation Stability A blonding cream was produced from the listed ingredients:

| Raw material | wt % |
|---|---|
| Hydrenol D | 12.00 |
| Lorol tech. | 2.40 |
| Texapon NSO | 26.50 |
| Stabylen 30 | 0.10 |
| Cetiol OE | 2.40 |
| Turpinal SL | 0.20 |
| Substantive DZ | 2.00 |
| Sodium silicate 40/42 | 0.50 |
| Ammonium sulfate | 1.00 |
| Ammonia, 25% | 7.60 |
| Water | ad 100 |

Hydrenol® D (INCI name: Cetearyl alcohol) (Cognis)

Lorol® tech. INCI name: Coconut alcohol (Cognis)

Texapon® NSO ca. 27.5% active substance; INCI name: Sodium Laureth Sulfate (Cognis)

Stabylen® 30 INCI name: Acrylates/Vinylisodecanoate Crosspolymer (3V Sigma)

Cetiol® OE INCI name: Dicaprylether (Cognis)

Turpinal® SL ca. 58-61% active substance content; INCI-name: Etidronic Acid, Aqua (Water)) (Solutia)

Hydrenol® D and Lorol® were melted together and Texapon® NSO, Stabylen® 30, Cetiol® OE and Turpinal® SL were then incorporated in that order with stirring. Sodium silicate 40/42 and ammonium sulfate were each dissolved in a small amount of water and likewise added with stirring. The inventive substantive was then dissolved in a small amount of water and likewise added to the formulation with stirring. The ammonia was then added at a temperature of 40° C. Water was then added with stirring to make up 100% and the formulation was stirred without heating.

Each blonding cream was blended in the ratio 1:1 with a developer dispersion formulated as follows:

| Raw material | wt % |
|---|---|
| Ammonia, 25% | 0.62 |
| Dipicolinic acid. | 0.10 |
| Disodium pyrophosphate | 0.03 |
| Turpinal SL | 1.50 |
| Texapon NSO | 2.040 |
| Dow Corning DB 110 A (non-ionic silicone emulsion) | 0.07 |

-continued

| Raw material | wt % |
|---|---|
| Aculyn 33A (acrylic polymer) | 12.00 |
| Hydrogen peroxide 50% | 22.40 |
| Water | ad 100 |

Aculyn ® 33A ca. 28% solids in water; INCI name: Acrylates Copolymer 100 g of the blonding cream were mixed with 100 g of the developer dispersion and 20 g of a mixture of ammonium peroxy disulfate, sodium peroxy disulfate and potassium peroxy disulfate (one part by weight of each). The pH of the finished formulation was between 9 and 10. 1.8 g of each of the finished application mixtures prepared in this manner were applied onto a ca. 6 cm long strand of human hair (Kerling Euronaturhaar, blonde) and left for 30 minutes at 30° C. At the end of the contact time the hair was rinsed out, washed with a conventional hair shampoo and then dried. The hair strands were dyed in the following listed nuances.

DZ 1: 1,4-Dimethyl-5-[(4-{ethyl[2-(4-aza-1-azoniabicyclo-[2.2.2]octan-1-yl)ethyl]-amino}phenyl)diazenyl]-4H-1,2,4-triazol-1-ium bis-p-toluene sulfonate (inventive)

DZ 2: 1-[2-({4-[2-(1,2,4-4H-triazol-3-yl)diazenyl]phenyl}ethylamino)ethyl]-4-aza-1-azoniabicyclo[2.2.2]octane, chloride (not inventive, product from synthesis example 1.3.)

| Dye | Color shade (intensity) without hydrogen peroxide/persulfate | Color shade (intensity) with hydrogen peroxide/persulfate |
|---|---|---|
| DZ 1 (inventive) | blood red (+++) | blood red (+++) |
| DZ 2 (comparative, non-inventive) | Indian yellow (+++) | weakly beige yellow |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the invention as set forth in the appended claims and their legal equivalents.

The invention claimed is:

1. An agent for dyeing and optionally simultaneously lightening keratin fibers, the agent comprising a dicationic azo dye of a Formula (I):

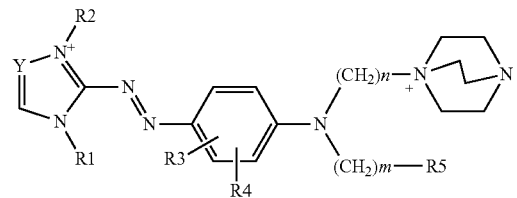

in which

Y is either for =CH— or a nitrogen atom, $R^1$ and $R^2$ independently of one another are a $C_1$-$C_6$ alkyl group, a $C_2$-$C_6$ alkenyl group, a hydroxy $C_1$-$C_6$ alkyl group, a polyhydroxy $C_2$-$C_6$ alkyl group, a $C_1$-$C_6$ alkoxy $C_2$-$C_6$ alkyl group, a cyano $C_1$-$C_6$ alkyl group, an aryl group or an aryl $C_1$-$C_6$ alkyl group, $R^3$ and $R^4$ independently of one another are a hydrogen atom, a $C_1$-$C_6$ alkyl group, a fluorine, chlorine, bromine or iodine halogen atom, a $C_1$-$C_6$ alkoxy group, an amino group, a $C_1$-$C_6$ alkylamino group, a di-$C_1$-$C_6$ alkylamino group, a hydroxyl group or that $R^3$ and $R^4$ together form a 5-, 6- or 7-membered, saturated or unsaturated ring that can optionally comprise additional heteroatoms or can carry additional substituents, n and m independently of one another are a whole number from 1 to 6, $R^5$ is a hydrogen atom, a $C_1$-$C_6$ alkoxy group, a fluorine, chlorine, bromine or iodine halogen atom, a hydroxyl group, a $C_1$-$C_6$ alkoxy $C_2$-$C_6$ alkyloxy group, a nitrile group, an aryl group or a heteroaryl group, $X^-$ is a monovalent anion.

2. The agent according to claim 1, wherein $X^-$ is a halide, hydrogen sulfate, ½ sulfate, benzene sulfonate, p-toluene sulfonate, acetate, citrate, lactate, tetrafluoroborate, trifluoromethane sulfonate, or hexafluorophosphate.

3. The agent according to claim 1, wherein the agent comprises compounds of the Formula (I), in which $R^1$ and $R^2$ are the $C_1$-$C_6$ alkyl group, the $C_2$-$C_6$ alkenyl group or the aryl $C_1$-$C_6$ alkyl group.

4. The agent according to claim 3, wherein $R^1$ and $R^2$ are both a methyl or ethyl group, an allyl group or a benzyl group.

5. The agent according to claim 1, wherein the agent comprises a cationic compound from a group of the dicationic azo dyes formed from one chosen from:

Salts of 1,4-dimethyl-5-[(4-{methyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(4-{propyl[2-(4-aza-1-azoniabicyclo[2.2.2]octan-1-yl)ethyl]amino}phenyl)diazenyl]-4H-1,2,4-triazol-1-ium;

Salts of 1,4-diethyl-5-[(4-{methyl[2-(4-aza-1-azoniabicyclo[2.2.2]octan-1-yl)ethyl]amino}phenyl)diazenyl]-4H-1,2,4-triazol-1-ium;

Salts of 1,4-diethyl-5-[(4-{ethyl[2-(4-aza-1-azoniabicyclo[2.2.2]octan-1-yl)ethyl]amino}phenyl)diazenyl]-4H-1,2,4-triazol-1-ium;

Salts of 1,4-diethyl-5-[(4-{propyl[2-(4-aza-1-azoniabicyclo[2.2.2]octan-1-yl)ethyl]amino}phenyl)diazenyl]-4H-1,2,4-triazol-1-ium;

Salts of 1,4-diallyl-5-[(4-{methyl[2-(4-aza-1-azoniabicyclo[2.2.2]octan-1-yl)ethyl]amino}phenyl)diazenyl]-4H-1,2,4-triazol-1-ium;

Salts of 1,4-diallyl-5-[(4-{ethyl[2-(4-aza-1-azoniabicyclo[2.2.2]octan-1-yl)ethyl]amino}phenyl)diazenyl]-4H-1,2,4-triazol-1-ium;

Salts of 1,4-diallyl-5-[(4-{propyl[2-(4-aza-1-azoniabicyclo[2.2.2]octan-1-yl)ethyl]amino}phenyl)diazenyl]-4H-1,2,4-triazol-1-ium;

Salts of 1,4-dibenzyl-5-[(4-{methyl[2-(4-aza-1-azoniabicyclo[2.2.2]octan-1-yl)ethyl]amino}phenyl)diazenyl]-4H-1,2,4-triazol-1-ium;

Salts of 1,4-dibenzyl-5-[(4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dibenzyl-5-[(4-{propyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(2-methyl-4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(2-methoxy-4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(2-chloro-4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(4-{methyl[3-(4-aza-1-azoniabicyclo[2.2.2]octan-1-yl)propyl]amino}phenyl)diazenyl]-4H-1,2,4-triazol-1-ium;

Salts of 1,4-dimethyl-5-[(4-{ethyl[3-(4-aza-1-azoniabicyclo[2.2.2]octan-1-yl)propyl]amino}phenyl)diazenyl]-4H-1,2,4-triazol-1-ium;

Salts of 1,4-dimethyl-5-[(4-{propyl[3-(4-aza-1-azoniabicyclo[2.2.2]octan-1-yl)propyl]amino}phenyl)diazenyl]-4H-1,2,4-triazol-1-ium;

Salts of 1,4-diethyl-5-[(4-{methyl[3-(4-aza-1-azoniabicyclo[2.2.2]octan-1-yl)propyl]amino}phenyl)diazenyl]-4H-1,2,4-triazol-1-ium;

Salts of 1,4-diethyl-5-[(4-{ethyl[3-(4-aza-1-azoniabicyclo[2.2.2]octan-1-yl)propyl]amino}phenyl)diazenyl]-4H-1,2,4-triazol-1-ium;

Salts of 1,4-diethyl-5-[(4-{propyl[3-(4-aza-1-azoniabicyclo[2.2.2]octan-1-yl)propyl]amino}phenyl)diazenyl]-4H-1,2,4-triazol-1-ium;

Salts of 1,4-diallyl-5-[(4-{methyl[3-(4-aza-1-azoniabicyclo[2.2.2]octan-1-yl)propyl]amino}phenyl)diazenyl]-4H-1,2,4-triazol-1-ium;

Salts of 1,4-diallyl-5-[(4-{ethyl[3-(4-aza-1-azoniabicyclo[2.2.2]octan-1-yl)propyl]amino}phenyl)diazenyl]-4H-1,2,4-triazol-1-ium;

Salts of 1,4-diallyl-5-[(4-{propyl[3-(4-aza-1-azoniabicyclo[2.2.2]octan-1-yl)propyl]amino}phenyl)diazenyl]-4H-1,2,4-triazol-1-ium;

Salts of 1,4-dibenzyl-5-[(4-{methyl[3-(4-aza-1-azoniabicyclo[2.2.2]octan-1-yl)propyl]amino}phenyl)diazenyl]-4H-1,2,4-triazol-1-ium;

Salts of 1,4-dibenzyl-5-[(4-{ethyl[3-(4-aza-1-azoniabicyclo[2.2.2]octan-1-yl)propyl]amino}phenyl)diazenyl]-4H-1,2,4-triazol-1-ium; and Salts of 1,4-dibenzyl-5-[(4-{propyl[3-(4-aza-1-azoniabicyclo[2.2.2]octan-1-yl)propyl]amino}phenyl)diazenyl]-4H-1,2,4-triazol-1-ium.

6. The agent according to claim 1, wherein the agent comprises a cationic compound from the group of the dicationic azo dyes which is formed from one chosen from:

Salts of 1,3-dimethyl-2-[(4-{methyl[2-(4-aza-1-azoniabicyclo[2.2.2]octan-1-yl)ethyl]amino}phenyl)diazenyl]-1H-imidazol-3-ium;

Salts of 1,3-dimethyl-2-[(4-{ethyl[2-(4-aza-1-azoniabicyclo[2.2.2]octan-1-yl)ethyl]amino}phenyl)diazenyl]-1H-imidazol-3-ium;

Salts of 1,3-dimethyl-2-[(4-{propyl[2-(4-aza-1-azoniabicyclo[2.2.2]octan-1-yl)ethyl]amino}phenyl)diazenyl]-1H-imidazol-3-ium;

Salts of 1,3-diethyl-2-[(4-{methyl[2-(4-aza-1-azoniabicyclo[2.2.2]octan-1-yl)ethyl]amino}phenyl)diazenyl]-1H-imidazol-3-ium;

Salts of 1,3-diethyl-2-[(4-{ethyl[2-(4-aza-1-azoniabicyclo[2.2.2]octan-1-yl)ethyl]amino}phenyl)diazenyl]-1H-imidazol-3-ium;

Salts of 1,3-diethyl-2-[(4-{propyl[2-(4-aza-1-azoniabicyclo[2.2.2]octan-1-yl)ethyl]amino}phenyl)diazenyl]-1H-imidazol-3-ium;

Salts of 1,3-diallyl-2-[(4-{methyl[2-(4-aza-1-azoniabicyclo[2.2.2]octan-1-yl)ethyl]amino}phenyl)diazenyl]-1H-imidazol-3-ium;

Salts of 1,3-diallyl-2-[(4-{ethyl[2-(4-aza-1-azoniabicyclo[2.2.2]octan-1-yl)ethyl]amino}phenyl)diazenyl]-1H-imidazol-3-ium;

Salts of 1,3-diallyl-2-[(4-{propyl[2-(4-aza-1-azoniabicyclo[2.2.2]octan-1-yl)ethyl]amino}phenyl)diazenyl]-1H-imidazol-3-ium;

Salts of 1,3-dibenzyl-2-[(4-{methyl[2-(4-aza-1-azoniabicyclo[2.2.2]octan-1-yl)ethyl]amino}phenyl)diazenyl]-1H-imidazol-3-ium;

Salts of 1,3-dibenzyl-2-[(4-{ethyl[2-(4-aza-1-azoniabicyclo[2.2.2]octan-1-yl)ethyl]amino}phenyl)diazenyl]-1H-imidazol-3-ium;

Salts of 1,3-dibenzyl-2-[(4-{propyl[2-(4-aza-1-azoniabicyclo[2.2.2]octan-1-yl)ethyl]amino}phenyl)diazenyl]-1H-imidazol-3-ium;

Salts of 1,3-dimethyl-2-[(2-methyl-4-{ethyl[2-(4-aza-1-azoniabicyclo[2.2.2]octan-1-yl)ethyl]amino}phenyl)diazenyl]-1H-imidazol-3-ium;

Salts of 1,3-dimethyl-2-[(2-methoxy-4-{ethyl[2-(4-aza-1-azoniabicyclo[2.2.2]octan-1-yl)ethyl]amino}phenyl)diazenyl]-1H-imidazol-3-ium;

Salts of 1,3-dimethyl-2-[(2-chloro-4-{ethyl[2-(4-aza-1-azoniabicyclo[2.2.2]octan-1-yl)ethyl]amino}phenyl)diazenyl]-1H-imidazol-3-ium;

Salts of 1,3-dimethyl-2-[(4-{methyl[3-(4-aza-1-azoniabicyclo[2.2.2]octan-1-yl)propyl]amino}phenyl)diazenyl]-1H-imidazol-3-ium;

Salts of 1,3-dimethyl-2-[(4-{ethyl[3-(4-aza-1-azoniabicyclo[2.2.2]octan-1-yl)propyl]amino}phenyl)diazenyl]-1H-imidazol-3-ium;

Salts of 1,3-dimethyl-2-[(4-{propyl[3-(4-aza-1-azoniabicyclo[2.2.2]octan-1-yl)propyl]amino}phenyl)diazenyl]-1H-imidazol-3-ium;

Salts of 1,3-diethyl-2-[(4-{methyl[3-(4-aza-1-azoniabicyclo[2.2.2]octan-1-yl)propyl]amino}phenyl)diazenyl]-1H-imidazol-3-ium;

Salts of 1,3-diethyl-2-[(4-{ethyl[3-(4-aza-1-azoniabicyclo[2.2.2]octan-1-yl)propyl]amino}phenyl)diazenyl]-1H-imidazol-3-ium;

Salts of 1,3-diethyl-2-[(4-{propyl[3-(4-aza-1-azoniabicyclo[2.2.2]octan-1-yl)propyl]amino}phenyl)diazenyl]-1H-imidazol-3-ium;

Salts of 1,3-diallyl-2-[(4-{methyl[3-(4-aza-1-azoniabicyclo[2.2.2]octan-1-yl)propyl]amino}phenyl)diazenyl]-1H-imidazol-3-ium;

Salts of 1,3-diallyl-2-[(4-{ethyl[3-(4-aza-1-azoniabicyclo[2.2.2]octan-1-yl)propyl]amino}phenyl)diazenyl]-1H-imidazol-3-ium;

Salts of 1,3-diallyl-2-[(4-{propyl[3-(4-aza-1-azoniabicyclo[2.2.2]octan-1-yl)propyl]amino}phenyl)diazenyl]-1H-imidazol-3-ium;

Salts of 1,3-dibenzyl-2-[(4-{methyl[3-(4-aza-1-azoniabicyclo[2.2.2]octan-1-yl)propyl]amino}phenyl)diazenyl]-1H-imidazol-3-ium;

Salts of 1,3-dibenzyl-2-[(4-{ethyl[3-(4-aza-1-azoniabicyclo[2.2.2]octan-1-yl)propyl]amino}phenyl)diazenyl]-1H-imidazol-3-ium, and Salts of 1,3-dibenzyl-2-[(4-{propyl[3-(4-aza-1-azoniabicyclo[2.2.2]octan-1-yl)propyl]amino}phenyl)diazenyl]-1H-imidazol-3-ium.

7. The agent according to claim 1, wherein the agent comprises the dicationic azo dye of the Formula (I) in an amount of from about 0.001 to about 5 wt %, based on the total agent.

8. The agent according to claim 7, wherein the agent comprises the dicationic azo dye of the Formula (I) in an amount of from about 0.0025 to about 2.5 wt %, based on the total agent.

9. The agent according to claim 8, wherein the agent comprises the dicationic azo dye of the Formula (I) in an amount of from about 0.005 to about 1.5 wt %, based on the total agent.

10. The agent according to claim 9, wherein the agent comprises the dicationic azo dye of the Formula (I) in an amount of from about 0.01 to about 1 wt %, based on the total agent, based on the total agent.

11. The according to claim 1, wherein the agent additionally comprises, based on its weight, about 0.001 to about 5 wt % of an oxidation dye precursor and/or a substantive dye.

12. The agent according to claim 1, wherein the agent comprises about 0.5 to about 15 wt % of hydrogen peroxide (calculated as 100% conc. $H_2O_2$).

13. The agent according to claim 12, wherein the agent comprises about 1 to about 12.5 wt % of hydrogen peroxide (calculated as 100% conc. $H_2O_2$).

14. The agent according to claim 13, wherein the agent comprises about 2.5 to about 10 wt % of hydrogen peroxide (calculated as 100% conc. $H_2O_2$).

15. The agent according to claim 14, wherein the agent comprises about 3 to about 6 wt % of hydrogen peroxide (calculated as 100% conc. $H_2O_2$).

16. The agent according to claim 1, wherein the agent is an agent for dyeing and optionally simultaneously lightening human hair.

17. A method for dyeing and optionally simultaneously lightening keratinic fibers, the method comprising the steps of:

optionally, depositing a pre-treatment agent M1 onto the keratinic fibers;

optionally, adding an agent M3 to an agent M2;

applying the agent M2 on the keratinic fibers;

rinsing the agent M2 out of the keratinic fibers after about 5 to about 30 minutes;

optionally applying a post-treatment agent M4 onto the keratinic fibers and rinsing out from the keratinic fibers after a predetermined contact time, wherein at least one of the pre-treatment agent M1, the agent M2 or the agent M3 is an agent comprising a dicationic azo dye of a Formula (I):

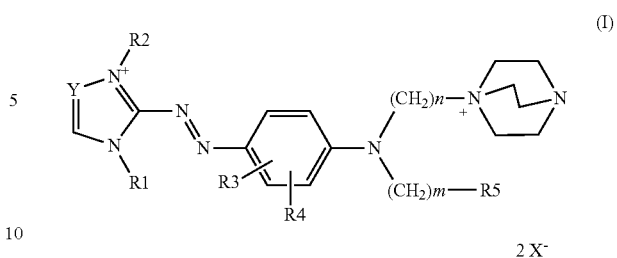

in which
Y is either for =CH— or a nitrogen atom,
$R^1$ and $R^2$ independently of one another are a $C_1$-$C_6$ alkyl group, a $C_2$-$C_6$ alkenyl group, a hydroxy $C_1$-$C_6$ alkyl group, a polyhydroxy $C_2$-$C_6$ alkyl group, a $C_1$-$C_6$ alkoxy $C_2$-$C_6$ alkyl group, a cyano $C_1$-$C_6$ alkyl group, an aryl group or an aryl $C_1$-$C_6$ alkyl group,
$R^3$ and $R^4$ independently of one another are a hydrogen atom, a $C_1$-$C_6$ alkyl group, a fluorine, chlorine, bromine or iodine halogen atom, a $C_1$-$C_6$ alkoxy group, an amino group, a $C_1$-$C_6$ alkylamino group, a di-$C_1$-$C_6$ alkylamino group, a hydroxyl group or that $R^3$ and $R^4$ together form a 5-, 6- or 7-membered, saturated or unsaturated ring that can optionally comprise additional heteroatoms or can carry additional substituents,
n and m independently of one another are a whole number from 1 to 6,
$R^5$ is a hydrogen atom, a $C_1$-$C_6$ alkoxy group, a fluorine, chlorine, bromine or iodine halogen atom, a hydroxyl group, a $C_1$-$C_6$ alkoxy $C_2$-$C_6$ alkyloxy group, a nitrile group, an aryl group or a heteroaryl group,
$X^-$ is a monovalent anion.

18. The method according to claim 17, wherein applying the agent M2 on the keratinic fibers comprises applying the agent M2 on human hair.

19. A dicationic azo dye of a Formula (I):

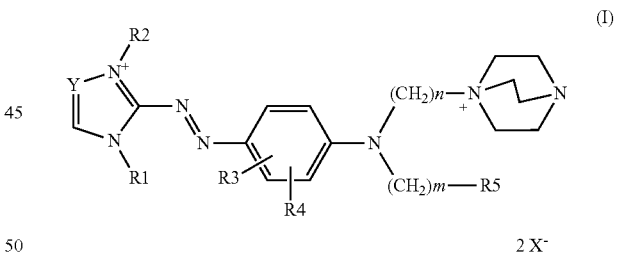

in which
Y is either for =CH— or a nitrogen atom,
$R^1$, $R^2$ independently of one another are a $C_1$-$C_6$ alkyl group, a $C_2$-$C_6$ alkenyl group, a hydroxy $C_1$-$C_6$ alkyl group, a polyhydroxy $C_2$-$C_6$ alkyl group, a $C_1$-$C_6$ alkoxy $C_2$-$C_6$ alkyl group, a cyano $C_1$-$C_6$ alkyl group, an aryl group or an aryl $C_1$-$C_6$ alkyl group,
$R^3$ and $R^4$ independently of one another are a hydrogen atom, a $C_1$-$C_6$ alkyl group, a fluorine, chlorine, bromine or iodine halogen atom, a $C_1$-$C_6$ alkoxy group, an amino group, a $C_1$-$C_6$ alkylamino group, a di-$C_1$-$C_6$ alkylamino group, a hydroxyl group or that $R^3$ and $R^4$ together form a 5-, 6- or 7-membered, saturated or unsaturated ring that can optionally comprise additional heteroatoms or can carry additional substituents, n and m independently of one another are a whole number from 1 to 6, $R^5$ is a hydrogen atom, a $C_1$-$C_6$ alkoxy group, a fluorine, chlorine, bromine or iodine halogen atom, a hydroxyl group, a $C_1$-$C_6$ alkoxy $C_2$-$C_6$ alkyloxy group, a nitrile group, an aryl group or a heteroaryl group, $X^-$ is a monovalent anion.

20. The dicationic azo dye according to claim 19, wherein the dicationic azo dye is selected from:

Salts of 1,4-dimethyl-5-[(4-{methyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(4-{propyl[2-(4-aza-1-azoniabicyclo[2.2.2]octan-1-yl)ethyl]amino}phenyl)diazenyl]-4H-1,2,4-triazol-1-ium;

Salts of 1,4-diethyl-5-[(4-{methyl[2-(4-aza-1-azoniabicyclo[2.2.2]octan-1-yl)ethyl]amino}phenyl)diazenyl]-4H-1,2,4-triazol-1-ium;

Salts of 1,4-diethyl-5-[(4-{ethyl[2-(4-aza-1-azoniabicyclo[2.2.2]octan-1-yl)ethyl]amino}phenyl)diazenyl]-4H-1,2,4-triazol-1-ium;

Salts of 1,4-diethyl-5-[(4-{propyl[2-(4-aza-1-azoniabicyclo[2.2.2]octan-1-yl)ethyl]amino}phenyl)diazenyl]-4H-1,2,4-triazol-1-ium;

Salts of 1,4-diallyl-5-[(4-{methyl[2-(4-aza-1-azoniabicyclo[2.2.2]octan-1-yl)ethyl]amino}phenyl)diazenyl]-4H-1,2,4-triazol-1-ium;

Salts of 1,4-diallyl-5-[(4-{ethyl[2-(4-aza-1-azoniabicyclo[2.2.2]octan-1-yl)ethyl]amino}phenyl)diazenyl]-4H-1,2,4-triazol-1-ium;

Salts of 1,4-diallyl-5-[(4-{propyl[2-(4-aza-1-azoniabicyclo[2.2.2]octan-1-yl)ethyl]amino}phenyl)diazenyl]-4H-1,2,4-triazol-1-ium;

Salts of 1,4-dibenzyl-5-[(4-{methyl[2-(4-aza-1-azoniabicyclo[2.2.2]octan-1-yl)ethyl]amino}phenyl)diazenyl]-4H-1,2,4-triazol-1-ium;

Salts of 1,4-dibenzyl-5-[(4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dibenzyl-5-[(4-{propyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(2-methyl-4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(2-methoxy-4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(2-chloro-4-{ethyl[2-(4-aza-1-azoniabicyclo[2.2.2]octan-1-yl)ethyl]amino}phenyl)diazenyl]-4H-1,2,4-triazol-1-ium;

Salts of 1,4-dimethyl-5-[(4-{methyl[3-(4-aza-1-azoniabicyclo[2.2.2]octan-1-yl)propyl]amino}phenyl)diazenyl]-4H-1,2,4-triazol-1-ium;

Salts of 1,4-dimethyl-5-[(4-{ethyl[3-(4-aza-1-azoniabicyclo[2.2.2]octan-1-yl)propyl]amino}phenyl)diazenyl]-4H-1,2,4-triazol-1-ium;

Salts of 1,4-dimethyl-5-[(4-{propyl[3-(4-aza-1-azoniabicyclo[2.2.2]octan-1-yl)propyl]amino}phenyl)diazenyl]-4H-1,2,4-triazol-1-ium;

Salts of 1,4-diethyl-5-[(4-{methyl[3-(4-aza-1-azoniabicyclo[2.2.2]octan-1-yl)propyl]amino}phenyl)diazenyl]-4H-1,2,4-triazol-1-ium;

Salts of 1,4-diethyl-5-[(4-{ethyl[3-(4-aza-1-azoniabicyclo[2.2.2]octan-1-yl)propyl]amino}phenyl)diazenyl]-4H-1,2,4-triazol-1-ium;

Salts of 1,4-diethyl-5-[(4-{propyl[3-(4-aza-1-azoniabicyclo[2.2.2]octan-yl)propyl]amino}phenyl)diazenyl]-4H-1,2,4-triazol-1-ium;

Salts of 1,4-diallyl-5-[(4-{methyl[3-(4-aza-1-azoniabicyclo[2.2.2]octan-yl)propyl]amino}phenyl)diazenyl]-4H-1,2,4-triazol-1-ium;

Salts of 1,4-diallyl-5-[(4-{ethyl[3-(4-aza-1-azoniabicyclo[2.2.2]octan-yl)propyl]amino}phenyl)diazenyl]-4H-1,2,4-triazol-1-ium;

Salts of 1,4-diallyl-5-[(4-{propyl[3-(4-aza-1-azoniabicyclo[2.2.2]octan-yl)propyl]amino}phenyl)diazenyl]-4H-1,2,4-triazol-1-ium;

Salts of 1,4-dibenzyl-5-[(4-{methyl[3-(4-aza-1-azoniabicyclo[2.2.2]octan-yl)propyl]amino}phenyl)diazenyl]-4H-1,2,4-triazol-1-ium;

Salts of 1,4-dibenzyl-5-[(4-{ethyl[3-(4-aza-1-azoniabicyclo[2.2.2]octan-yl)propyl]amino}phenyl)diazenyl]-4H-1,2,4-triazol-1-ium;

Salts of 1,4-dibenzyl-5-[(4-{propyl[3-(4-aza-1-azoniabicyclo[2.2.2]octan-yl)propyl]amino}phenyl)diazenyl]-4H-1,2,4-triazol-1-ium;

Salts of 1,3-dimethyl-2-[(4-{methyl[2-(4-aza-1-azoniabicyclo[2.2.2]octan-yl)ethyl]amino}phenyl)diazenyl]-1H-imidazol-3-ium;

Salts of 1,3-dimethyl-2-[(4-{ethyl[2-(4-aza-1-azoniabicyclo[2.2.2]octan-yl)ethyl]amino}phenyl)diazenyl]-1H-imidazol-3-ium;

Salts of 1,3-dimethyl-2-[(4-{propyl[2-(4-aza-1-azoniabicyclo[2.2.2]octan-yl)ethyl]amino}phenyl)diazenyl]-1H-imidazol-3-ium;

Salts of 1,3-diethyl-2-[(4-{methyl[2-(4-aza-1-azoniabicyclo[2.2.2]octan-yl)ethyl]amino}phenyl)diazenyl]-1H-imidazol-3-ium;

Salts of 1,3-diethyl-2-[(4-{ethyl[2-(4-aza-1-azoniabicyclo[2.2.2]octan-yl)ethyl]amino}phenyl)diazenyl]-1H-imidazol-3-ium;

Salts of 1,3-diethyl-2-[(4-{propyl[2-(4-aza-1-azoniabicyclo[2.2.2]octan-yl)ethyl]amino}phenyl)diazenyl]-1H-imidazol-3-ium;

Salts of 1,3-diallyl-2-[(4-{methyl[2-(4-aza-1-azoniabicyclo[2.2.2]octan-yl)ethyl]amino}phenyl)diazenyl]-1H-imidazol-3-ium;

Salts of 1,3-diallyl-2-[(4-{ethyl[2-(4-aza-1-azoniabicyclo[2.2.2]octan-yl)ethyl]amino}phenyl)diazenyl]-1H-imidazol-3-ium;

Salts of 1,3-diallyl-2-[(4-{propyl[2-(4-aza-1-azoniabicyclo[2.2.2]octan-yl)ethyl]amino}phenyl)diazenyl]-1H-imidazol-3-ium;

Salts of 1,3-dibenzyl-2-[(4-{methyl[2-(4-aza-1-azoniabicyclo[2.2.2]octan-yl)ethyl]amino}phenyl)diazenyl]-1H-imidazol-3-ium;

Salts of 1,3-dibenzyl-2-[(4-{ethyl[2-(4-aza-1-azoniabicyclo[2.2.2]octan-yl)ethyl]amino}phenyl)diazenyl]-1H-imidazol-3-ium;

Salts of 1,3-dibenzyl-2-[(4-{propyl[2-(4-aza-1-azoniabicyclo[2.2.2]octan-yl)ethyl]amino}phenyl)diazenyl]-1H-imidazol-3-ium;

Salts of 1,3-dimethyl-2-[(2-methyl-4-{ethyl[2-(4-aza-1-azoniabicyclo[2.2.2]octan-1-yl)ethyl]amino}phenyl)diazenyl]-1H-imidazol-3-ium;

Salts of 1,3-dimethyl-2-[(2-methoxy-4-{ethyl[2-(4-aza-1-azoniabicyclo[2.2.2]octan-1-yl)ethyl]amino}phenyl)diazenyl]-1H-imidazol-3-ium;

Salts of 1,3-dimethyl-2-[(2-chloro-4-{ethyl[2-(4-aza-1-azoniabicyclo[2.2.2]octan-1-yl)ethyl]amino}phenyl)diazenyl]-1H-imidazol-3-ium;

Salts of 1,3-dimethyl-2-[(4-{methyl[3-(4-aza-1-azoniabicyclo[2.2.2]octan-1-yl)propyl]amino}phenyl)diazenyl]-1H-imidazol-3-ium;

Salts of 1,3-dimethyl-2-[(4-{ethyl[3-(4-aza-1-azoniabicyclo[2.2.2]octan-1-yl)propyl]amino}phenyl)diazenyl]-1H-imidazol-3-ium;

Salts of 1,3-dimethyl-2-[(4-{propyl[3-(4-aza-1-azoniabicyclo[2.2.2]octan-1-yl)propyl]amino}phenyl)diazenyl]-1H-imidazol-3-ium;

Salts of 1,3-diethyl-2-[(4-{methyl[3-(4-aza-1-azoniabicyclo[2.2.2]octan-1-yl)propyl]amino}phenyl)diazenyl]-1H-imidazol-3-ium;

Salts of 1,3-diethyl-2-[(4-{ethyl[3-(4-aza-1-azoniabicyclo[2.2.2]octan-1-yl)propyl]amino}phenyl)diazenyl]-1H-imidazol-3-ium;

Salts of 1,3-diethyl-2-[(4-{propyl[3-(4-aza-1-azoniabicyclo[2.2.2]octan-1-yl)propyl]amino}phenyl)diazenyl]-1H-imidazol-3-ium;

Salts of 1,3-diallyl-2-[(4-{methyl[3-(4-aza-1-azoniabicyclo[2.2.2]octan-1-yl)propyl]amino}phenyl)diazenyl]-1H-imidazol-3-ium;

Salts of 1,3-diallyl-2-[(4-{ethyl[3-(4-aza-1-azoniabicyclo[2.2.2]octan-1-yl)propyl]amino}phenyl)diazenyl]-1H-imidazol-3-ium;

Salts of 1,3-diallyl-2-[(4-{propyl[3-(4-aza-1-azoniabicyclo[2.2.2]octan-1-yl)propyl]amino}phenyl)diazenyl]-1H-imidazol-3-ium;

Salts of 1,3-dibenzyl-2-[(4-{methyl[3-(4-aza-1-azoniabicyclo[2.2.2]octan-1-yl)propyl]amino}phenyl)diazenyl]-1H-imidazol-3-ium;

Salts of 1,3-dibenzyl-2-[(4-{ethyl[3-(4-aza-1-azoniabicyclo[2.2.2]octan-1-yl)propyl]amino}phenyl)diazenyl]-1H-imidazol-3-ium, and Salts of 1,3-dibenzyl-2-[(4-{propyl[3-(4-aza-1-azoniabicyclo[2.2.2]octan-1-yl)propyl]amino}phenyl)diazenyl]-1H-imidazol-3-ium.

\* \* \* \* \*